United States Patent
Heinzerling et al.

(10) Patent No.: US 12,364,668 B2
(45) Date of Patent: Jul. 22, 2025

(54) TREATMENT OF OPIOID USE DISORDER, OPIOID WITHDRAWAL SYMPTOMS, AND CHRONIC PAIN

(71) Applicant: THE REGENTS OF THE UNIVERSITY OF CALIFORNIA, Oakland, CA (US)

(72) Inventors: Keith G. Heinzerling, Agoura Hills, CA (US); Marisa S. Briones, Sherman Oaks, CA (US); Dustin Z. Deyoung, Valley Village, CA (US)

(73) Assignee: The Regents of the University of California, Oakland, CA (US)

( * ) Notice: Subject to any disclaimer, the term of this patent is extended or adjusted under 35 U.S.C. 154(b) by 405 days.

(21) Appl. No.: 16/764,327

(22) PCT Filed: Nov. 15, 2018

(86) PCT No.: PCT/US2018/061293
§ 371 (c)(1),
(2) Date: May 14, 2020

(87) PCT Pub. No.: WO2019/099679
PCT Pub. Date: May 23, 2019

(65) Prior Publication Data
US 2020/0345655 A1    Nov. 5, 2020

Related U.S. Application Data

(60) Provisional application No. 62/586,636, filed on Nov. 15, 2017.

(51) Int. Cl.
| | | |
|---|---|---|
| *A61K 31/05* | (2006.01) | |
| *A61K 9/00* | (2006.01) | |
| *A61K 9/20* | (2006.01) | |
| *A61K 9/48* | (2006.01) | |
| *A61K 9/70* | (2006.01) | |
| *A61K 31/485* | (2006.01) | |
| *A61K 36/185* | (2006.01) | |
| *A61P 25/36* | (2006.01) | |

(52) U.S. Cl.
CPC .............. *A61K 31/05* (2013.01); *A61K 9/006* (2013.01); *A61K 9/20* (2013.01); *A61K 9/48* (2013.01); *A61K 9/7023* (2013.01); *A61K 31/485* (2013.01); *A61K 36/185* (2013.01); *A61P 25/36* (2018.01); *A61K 2236/30* (2013.01)

(58) Field of Classification Search
None
See application file for complete search history.

(56) References Cited

U.S. PATENT DOCUMENTS

| | | | |
|---|---|---|---|
| 3,773,955 A | 11/1973 | Pachter et al. | |
| 4,457,933 A | 7/1984 | Gordon et al. | |
| 4,464,378 A * | 8/1984 | Hussain | A61K 31/485 546/61 |
| 4,661,492 A | 4/1987 | Lewi et al. | |
| 7,671,052 B2 | 3/2010 | Dolle et al. | |
| 2008/0058302 A1 | 3/2008 | Dolle et al. | |
| 2009/0029984 A1* | 1/2009 | Adam-Worrall | A61K 31/4468 514/648 |
| 2009/0311347 A1* | 12/2009 | Oronsky | A61P 25/36 424/722 |
| 2011/0097395 A1 | 10/2011 | Babul et al. | |
| 2011/0245783 A1* | 10/2011 | Stinchcomb | A61P 25/30 156/60 |
| 2018/0110730 A1* | 4/2018 | Changoer | A61K 31/352 |

FOREIGN PATENT DOCUMENTS

| | | |
|---|---|---|
| CN | 103813785 | 5/2014 |
| WO | WO 2009/114118 A2 | 9/2009 |
| WO | WO 2018/075665 A1 | 4/2018 |
| WO | WO 2018/211388 A1 | 11/2018 |

OTHER PUBLICATIONS

Chaudhary et al., Medicated chewing gum—a potential drug delivery system, Expert Opin Drug Deliv. Jul. 2010;7(7):871-85.*
Karschner et al., Subjective and Physiological Effects After Controlled Sativex and Oral THC Administration, Clin Pharmacol Ther. Mar. 2011; 89(3): 10.*
Gorden et al., Buprenorphine for Opioid Dependence, Interventions for Addiction 2013, available at https://www.sciencedirect.com/topics/neuroscience/buprenorphine.*
Johnson et al., Multicenter, double-blind, randomized, placebo-controlled, parallel-group study of the efficacy, safety, and tolerability of THC:CBD extract and THC extract in patients with intractable cancer-related pain. J Pain Symptom Manag. 2010;39:167-79.*
Portenoy RK et al,. Nabiximols for opioid-treated cancer patients with poorly-controlled chronic pain: a randomized, placebo-controlled, graded-dose trial. J Pain. 2012;13:438-49.*
Narang et al., Efficacy of dronabinol as an adjuvant treatment for chronic pain patients on opioid therapy. J Pain. 2008;9:254-64.*
Cichewicz D L et al., Enhancement of transdermal fentanyl and buprenorphine antinociception by transdermal Delta$^9$-tetrahydrocannabinol. *European Journal of Pharmacology*, 525, pp. 74-82 (2005).

(Continued)

*Primary Examiner* — Svetlana M Ivanova
(74) *Attorney, Agent, or Firm* — Norton Rose Fulbright US LLP

(57) ABSTRACT

The current methods and compositions provide for a novel and effective therapeutic method for treating opioid use disorder, opioid withdrawal symptoms and/or chronic pain. Accordingly, certain aspects of the disclosure relate to a method for treating opioid use disorder, opioid withdrawal symptoms and/or chronic pain in a subject, the method comprising administering at least one purified cannabinoid compound and a partial opioid agonist. In some embodiments, the method comprises administering a composition comprising cannabidiol and buprenorphine.

22 Claims, 5 Drawing Sheets

(56) References Cited

OTHER PUBLICATIONS

European Supplementary Search Report dated Jul. 14, 2021 issued in European Patent Application No. 18878441.7.
Chinese Office Action and Search Report in corresponding Chinese Application No. 20188081027.4, dated Feb. 8, 2022.
Chaudhary et al., Directly comprehensible medicated chewing gum formulation for quick relief from common cold. *International Journal of Pharmaceutical Investigation*, 2(3):123-133. 2012.
Abuse-Deterrent Opioids—Evaluation and Labeling, Guidance for Industry. *U.S. Department of Health and Human Services, Food and Drug Administration, Center for Drug Evaluation and Research*, Apr. 2012.
Hua, Susan, Advances in Nanoparticulate Drug Delivery Approaches for Sublingual and Buccal Administration. *Frontiers on Pharmacology*, 10(1328):1-9, 2019.
Lipp, Ralph, Innovative Abuse-Deterrent Opioid Medications. *American Pharmaceutical Review*, 2016.
Jhanwar, et al., Chewing Gum: Confectionary to a Popular Transbuccal Dosage Form. *Asian Journal of Pharmaceutical and Clinical Research*, 10(6) 2017.
Rathbone et al., eds. Anatomy and Physiology of the Oral Mucosa, *Oral Mucosal Drug Delivery and Therapy, Springer New York Heidelberg Dordrecht London*, Chapter 1, 2015.
Route of Administration, https://www.fda.gov/drugs/data-standards-manual-monographs/route-administration.
Sheldon, et al., Early abortion with buccal versus sublingual misoprostol alone: a multicenter, randomized trial. *Contraception Journal*, 99(5):272-277, 2019.
Shiffman et al., Nicotine delivery systems. *Expert Opinion on Drug Delivery*, 2(3):563-577, 2005.
Silva-Abreu, et al., Comparative Study of Ex Vivo Transmucosal Permeation of Pioglitazone Nanoparticles for the Treatment of Alzheimer's Disease. *Polymers*, 10(316):pp. 1-13, 2018.
Arteta et al., "Evaluation of How Depression and Anxiety Mediate the Relationship Between Pain Catastrophizing and Prescription Opioid Misuse in a Chronic Pain Population"., *Pain Med*, 17(2): 295-303, 2016.
Babu et al., "Opioid receptors and legal highs: Salvia divinorum and Kratom", *Clin Toxicol (Phila)*,46(2):146-52, 2008.
Christoph et al., "Broad analgesic profile of buprenorphine in rodent models of acute and chronic pain", *Eur J Pharmacol*, 507(1-3): 87-98, 2005.
Costa et al., "The non-psychoactive cannabis constituent cannabidiol is an orally effective therapeutic agent in rat chronic inflammatory and neuropathic pain." *Eur J Pharmacol*, 556(1-3): 75-83, 2007.
Crippa et al., "Effects of cannabidiol (CBD) on regional cerebral blood flow." *Neuropsychopharmacology*, 29(2): 417-426, 2004.
Crippa et al., "Neural basis of anxiolytic effects of cannabidiol (CBD) in generalized social anxiety disorder: a preliminary report." *J Psychopharmacol*, 25(1): 121-130, 2011.
Cunningham et al., "Benzodiazepine use in patients with chronic pain in an interdisciplinary pain rehabilitation program." *J Pain Res*, 10: 311-317, 2017.
Edwards et al., "Changes in Pain Sensitivity and Pain Modulation During Oral Opioid Treatment: The Impact of Negative Affect." *Pain Medicine*, 17(10): 1882-1891, 2016.
Garg et al., "Patterns of Opioid Use and Risk of Opioid Overdose Death Among Medicaid Patients." *Med Care*, 55(7): 661-668, 2017.
Graham et al., "Cardiovascular and respiratory effects of cannabis in cat and rat." *Br J Pharmacol*, 49(1): 1-10, 1973.
Gureje et al., "Persistent pain and well-being: A world health organization study in primary care." *JAMA*, 280(2): 147-151.
International Preliminary Report on Patentability Issued in corresponding International application No. PCT/US2018/061293 mailed on Feb. 1, 2019.
International Search Report and Written Opinion issued in corresponding International application No. PCT/US18/61293 mailed on Feb. 1, 2019.
Kim et al., "The Concentration of Opioid Prescriptions by Providers and Among Patients in the Oregon Medicaid Program." *Psychiatr Serv*, 67(4): 397-404, 2016.
Larochelle et al., "Trends in opioid prescribing and co-prescribing of sedative hypnotics for acute and chronic musculoskeletal pain: 2001-2010." *Pharmacoepidemiol Drug Saf*, 24(8): 885-892, 2015.
Martel et al., "Catastrophic thinking and increased risk for prescription opioid misuse in patients with chronic pain." *Drug Alcohol Depend*, 132(1-2): 335-341, 2013.
Martins et al., "Changes in US Lifetime Heroin Use and Heroin Use Disorde: Prevalence From the 2001-2002 to 2012-2013 National Epidemiologic Survey on Alcohol and Related Conditions.", *JAMA Psychiatry*, 74(5):445-455, 2017.
McHugh et al., "Distress Intolerance and Prescription Opioid Misuse Among Patients With Chronic Pain." *J Pain*, 17(7): 806-814, 2016.
Nielsen et al., "Benzodiazepine use among chronic pain patients prescribed opioids: associations with pain, physical and mental health, and health service utilization." *Pain Med*, 16(2): 356-366, 2015.
Pisanti et al., "Cannabidiol: State of the art and new challenges for therapeutics applications." *Pharmacol Ther.*, 175: 133-150, 2017.
Stout et al.. "Exogeneous cannabinoids as substrates, inhibitors and inducers of human drug metabolizing enzymes: a systematic review." *Drug Metab Rev*, 46(1): 86-95, 2014.
Terry et al., "Pain Catastrophizing and Anxiety are Associated with Heat Pain Perception in a Community Sample of Adults With Chronic Pain." *Clin J Pain*, 32(10): 875-881, 2016.
Toth et al., "National and Northern New England Opioid Prescribing Patterns, 2013-2014." *Pain Med*, 18(9): 1706-1714, 2017.
Velly et al., "Epidemiology of pain and relation to psychiatric disorders." *Prog Neuropsychopharmacol Biol Psychiatry*, 87(Pt B): 159-167.
Wasan et al., "Psychiatric Comorbidity Is Associated Prospectively with Diminished Opioid Analgesia and Increased Opioid Misuse in Patients with Chronic Low Back Pain." *Anesthesiology*, 123(4): 861-872.
Wertli et al., "Catastrophizing-a prognostic factor for outcome in patients with low back pain: a systematic review." *Spine J.*, 14(11): 2639-2657, 2014.
Wikipedia, "Butorphanol", Oct. 14, 2016, retrieved on Jan. 18, 2019 from https://en.wikipedia.org/w/index.php?title=Butorphanol&oldid=744304035.
Wikipedia, "Cannabidiol", Nov. 5, 2017, retrieved on Jan. 17, 2019 from https://en.wikipedia.org/w/index.php?title=Cannabidiol&oldid=808773756.
Wikipedia, "levonantradol", Feb. 14, 2016, retrieved on Jan. 18, 2019 from https://en.wikipedia.org/w/index.php?title=Levonantradol&oldid=704990525.
Yoram et al., "Ultra-Low-Dose_Buprenorphine as a Time-Limited Treatment for Severe Suicidal Ideation: A Randomized Controlled Trial." American Journal of Psychiatry, 173(5): 491-498, 2016.
Zuardi et al., "Inverted U-Shaped Dose-Response Curve of the Anxioloytic Effect of Cannabidiol during Public Speaking in Real Life." Front Pharmcol, 8: 259, 2017.

\* cited by examiner

| Day | Von Frey Test | CBD/ Saline | BUP/ Saline | Neuropathic Pain Model |
|---|---|---|---|---|
| -1 | X | | | *Baseline* |
| 0 | ← | ← | ← | Sciatic nerve ligation (CCI model) |
| 1 | | | | *Development of chronic pain (CCI)* |
| 2 | | | | *Development of chronic pain (CCI)* |
| 3 | | | | *Development of chronic pain (CCI)* |
| 4 | | | | *Development of chronic pain (CCI)* |
| 5 | | | | *Development of chronic pain (CCI)* |
| 6 | | | | *Development of chronic pain (CCI)* |
| 7 | X | X | | |
| 8 | | X | | |
| 9 | | X | | |
| 10 | | X | | |
| 11 | | X | | |
| 12 | | X | | |
| 13 | | X | | |
| 14 | X | X | X | |

FIG. 4

TREATMENT OF OPIOID USE DISORDER, OPIOID WITHDRAWAL SYMPTOMS, AND CHRONIC PAIN

CROSS-REFERENCE TO RELATED APPLICATIONS

This application is a national phase application under 35 U.S.C. § 371 of International Application No PCT/US2018/061293, filed Nov. 15, 2018, which claims benefit of priority of U.S. Provisional Patent Application No. 62/586,636 filed Nov. 15, 2017, which is hereby incorporated by reference in its entirety

BACKGROUND OF THE INVENTION

1. Field of the Invention

Embodiments are directed generally to biology and medicine. In certain aspects methods involve treating opioid use disorder, opioid withdrawal symptoms and/or chronic pain in a patient. In additional embodiments there are therapeutic compositions and the use of such compositions for the treatment of opioid use disorder, opioid withdrawal symptoms and/or chronic pain.

2. Background Art

According to a 2015 study by the National Institutes of Health, nearly 50 million adults in the US have chronic or severe pain with over 25 million American adults reporting chronic daily pain in the past 3 months. Opioid prescribing for chronic pain has increased dramatically with 259 million opioid prescriptions filled in the US in 2012, which is more than enough to give every American adult their own prescription. Opioid prescribing rates among adolescents and young adults nearly doubled from 1994 to 2007. Currently the U.S. market for opioids for chronic pain management is estimated to be $10 billion.

The massive increase in opioid prescribing has contributed to an epidemic of opioid abuse especially among patients with chronic pain. According to results from the National Survey on Drug Use and Health (2015), an estimated 3.8 million people aged 12 years or older reported past month use or misuse (not directed by a physician) of opioid pain relievers. Another 329,000 people aged 12 or older reported past month heroin use. Approximately 2 million adults met criteria for opioid use disorder in 2015. Along with an increase in opioid use disorders, a rise in opioid-related overdose deaths has occurred in the last decade reaching a public health crisis. Rates of fatal overdose have skyrocketed surpassing deaths from motor vehicle accidents in the US. Drug overdose is the leading cause of accidental death in the US, with 55,403 lethal drug overdoses in 2015, and increased opioid prescribing and opioid addiction is driving this epidemic with 20,101 overdose deaths related to prescription pain relievers. Overdose death rate in 2008 was nearly 4 times the 1999 rate. From 1999 to 2008, overdose death rates, sales, and substance use disorder treatment admissions related to prescription pain relievers increased in parallel. Use of opioids with sedatives is particularly dangerous with 6.4 times the risk of overdose for opioids with sedatives and 12.6 times the risk of overdose for opioids with both benzodiazepines and muscle relaxants compared to opioids alone (Garg, Fulton-Kehoe et al. 2017). As awareness of prescription opioid overdose has increased, opioid prescribing appears to have plateaued (Toth, Possidente et al. 2016). Although as access to prescription opioids decreases, patients are increasingly switching to illicit opioids especially heroin (Martins, Sarvet et al. 2017). The US market for medications to treat opioid addiction is estimated to be at least $1.5 billion and likely to grow as more patients with chronic pain and opioid problems seek treatment despite significant drawbacks with existing opioid formulations including risk of addiction and overdose.

Anxiety and depression are common among patients with chronic pain and are risk factors for prescription opioid abuse and overdose (Velly and Mohit. 2017). People with chronic pain are four times as likely to have anxiety or depression than those without chronic pain (Gureje et al., 1998). In one sample of patients on opioids for chronic pain, 37% met criteria for an anxiety disorder and 34% for depression (Saffier et al., 2007). Co-prescribing of opioids and sedatives-hypnotics, a major risk factor for overdose, is common among patients with chronic pain and anxiety/depression with opioids and sedatives co-prescribed at 36% of visits for chronic musculoskeletal pain (Larochelle, Zhang et al. 2015). Opioid-benzodiazepine co-prescribing in chronic pain is most frequent among patients prescribed the highest opioid doses (Kim, Hartung et al. 2016) further increasing overdose risk. Use of benzodiazepines in chronic pain is associated with higher levels of pain intensity and interference, depression, and pain catastrophizing (Nielsen et al. 2015, Cunningham et al. 2017). Pain catastrophizing, a negative cognitive-affective response, including helplessness, rumination and magnification, to anticipated or actual pain is associated with increased risk of pain chronification, greater pain intensity and interference, more disability, and worse treatment outcomes in chronic pain (Wertli et al. 2014). Higher levels of pain catastrophizing and pain-related anxiety are associated with lower heat pain threshold and tolerance in patients with chronic pain (Terry et al. 2016) while pain catastrophizing, depression, and anxiety are associated with prescription opioid misuse among chronic pain patients (Martel et al. 2013; Arteta et al., 2016). Similar to catastrophizing, distress intolerance, the inability to handle aversive somatic or emotional states, is also associated with prescription opioid misuse in patients with chronic pain (McHugh et al. 2016). Negative affect, a cluster of negative emotions and thoughts manifesting as high levels of depression, anxiety, and catastrophizing is common in chronic pain. Negative affect is associated with lower opioid analgesia, higher opioid doses, increased rates of opioid misuse, and increased risk for the development of opioid-induced hyperalgesia among patients treated with opioids for chronic low back pain (Wasan et al. 2015; Dolman et al., 2016). Together, these studies demonstrate how the affective aspects of the chronic pain syndrome, including the associated depression, anxiety, and pain catastrophizing, have a major influence on important clinical variables.

Buprenorphine (BUP) and buprenorphine in combination with naloxone are currently FDA-approved in a variety of formulations for sublingual administration for the treatment of opioid use disorder, opioid withdrawal, and chronic pain. Current FDA-approved buprenorphine formulations for opioid use disorder contain buprenorphine in combination with the inactive ingredient naloxone which is included with the aim of deterring abuse of buprenorphine via the intravenous route. Buprenorphine is a partial opioid agonist that has a lower risk of overdose compared to full opioid agonists (e.g. morphine, hydrocodone, methadone, oxycodone) due to a "ceiling effect" on respiratory depression due to buprenorphine's activity as a partial opioid agonist. Despite this there remains a risk of overdose when buprenorphine is combined with sedatives including benzodiazepines and alcohol. Anxiety is frequently co-morbid with opioid use disorders and chronic pain conditions and is a core symptom of opioid withdrawal. Pain catastrophizing is associated with higher risk of prescription opioid abuse as well as worse clinical outcomes for pain management. Anxiety is a common trigger for opioid use and relapse among patients with opioid use disorders, opioid withdrawal, and chronic pain. As a result, despite the risks of overdose, opioids including buprenorphine are frequently prescribed with dangerous sedatives and anxiolytics including benzodiazepines and patients frequently abuse alcohol with opioids. Overdose due to opioids with sedatives including benzodiazepines play an important role in the current epidemic of opioid overdose deaths.

Chronic pain and opioid abuse are more prevalent than before constituting a public health crisis and exacting a heavy toll on patients, caregivers, physicians and society. There is a current therapeutic challenge for managing chronic pain, opioid use disorder, opioid withdrawal symptoms and/or associated anxiety and depression. A severe need remains for alternative and safe therapeutic regimens that properly treat these conditions.

SUMMARY OF THE INVENTION

A cannabinoid and partial opioid agonist combination treatment or combination formulation, as taught in the current disclosure, may be safer and more effective than currently existing options. The current methods and compositions provide therapeutic compositions and methods related to treating a patient who uses opioids or is in need of an opioid. In particular embodiments, there are compositions and methods for treating opioid use disorder, opioid withdrawal symptoms and/or chronic pain in a patient. In certain embodiments, the patient is at risk for opioid use disorder, opioid withdrawal symptoms, and/or chronic pain.

Accordingly, certain aspects of the disclosure relate to methods for treating opioid use disorder, treating opioid withdrawal symptoms, treating chronic pain, preventing opioid use disorder, preventing opioid withdrawal symptoms, treating or preventing anxiety, preventing opioid withdrawal, reducing the severity or duration of opioid withdrawal symptoms, reducing pain, reducing anxiety, preventing relapse of opioid use disorder or preventing opioid abuse; embodiments for these methods are disclosed throughout the disclosure. Any embodiment of one method can be implemented in the context of another embodiment discussed herein.

In certain embodiments, there are methods for treating a subject with opioid use disorder, opioid withdrawal symptoms, and/or chronic pain, the method comprising administering to the subject at least one purified cannabinoid compound and a partial opioid agonist. Without wishing to be bound by theory, it is believed that the use of a combination of cannabidiol and buprenorphine (or buprenorphine-naloxone), for example, is safer and more effective than either compound alone due to the combination of the anxiolytic effects of cannbidiol with the analgesic and anti-opioid craving/withdrawal effects of buprenorphine.

In certain embodiments, the subject is one determined to have opioid use disorder or suspected of using opioids. In further embodiments, the subject is a patient who will or has been prescribed opioids within 4 weeks. In other embodiments, the subject is a patient who will be or has been administered opioids within 4 weeks; the opioid(s) may be administered by the patient or by someone other than the patient, including a clinician. In certain embodiments, the subject has not been administered or has not administered any opioids to herself/himself for at least 6, 7, 8, 9, 10, 11, 12, 24 hours and/or 1, 2, 3, 4, 5, 6, 7 days and/1, 2, 3, 4 or more weeks (or any range derivable therein) prior to being administered any compound or composition discussed herein. In some embodiments, the subject has been opioid-free for a certain period of time before beginning treatment. In other embodiments, the subject is not opioid-free and the subject is administered treatment within 6, 7, 8, 9, 10, 11, 12, 24 hours and/or 1, 2, 3, 4, 5, 6, 7 days (or any range derivable therein) of having an opioid administered to or by the subject. It is specifically contemplated that the subject is a human subject or patient.

In some embodiments, the cannabinoid used in methods and/or compositions is a phytocannabinoid, while in other embodiments it is a synthetic cannabinoid. In some embodiments, the phytocannabinoid is derived from a *Cannabis* plant such as for example *Cannabis sativa*. In some embodiments, the phytocannabinoid is cannabidiol or cannabidivarin.

In some embodiments, the partial opioid agonist is buprenorphine, mitragynine or 7-hydroxymitragynine. In some embodiments, the partial opioid agonist is derived from *Mitragyna speciosa* ("Kratom").

In some embodiments, a purified cannabinoid and a partial opioid agonist are administered within 24 hours of each other. In some embodiments, at least one purified cannabinoid and the partial opioid agonist are administered within 6 hours of each other. In some embodiments, at least one purified cannabinoid and the partial opioid agonist are administered within 2 hours of each other. Yet in other embodiments, at least one purified cannabinoid and the partial opioid agonist are administered within 1 hour of each other. In some embodiments, at least one purified cannabinoid and the partial opioid agonist are administered within 30 minutes of each other. In some cases, a purified cannabinoid and the partial opioid agonist are administered at the same time to the subject. In some embodiments, the at least one purified cannabinoid and the partial opioid agonist are administered to the subject together in the same composition. In some embodiments of this method at least one purified cannabinoid compound is cannabidiol and/or the partial opioid agonist is buprenorphine.

Further aspects of the disclosure relate to methods further comprising administering an opioid antagonist to the subject. In some embodiments, the opioid antagonist is naloxone, an oxymorphol analog of naloxone, a naloxone salt, a naloxone dehydrate, naltrexone or nalmefene. In some embodiments, the opioid antagonist is naloxone. In some embodiments, the opioid antagonist is naltrexone.

Further aspects involve methods where the subject is a human. In some embodiments, the subject is a human diagnosed with an opioid use disorder, opioid withdrawal symptoms, and/or chronic pain. In some embodiments, the subject has been previously treated for opioid use disorder, opioid withdrawal symptoms and/or chronic pain.

In certain embodiments, a purified cannabinoid and/or the partial opioid agonist are administered in a composition that is a pharmaceutical formulation. In some embodiments, the cannabinoid is cannabidiol and the partial opioid agonist is buprenorphine. In some embodiments of this method, the composition further includes an opioid antagonist such as naloxone, an oxymorphol analogue of naloxone, a naloxone salt, a nalozone dehydrate, naltrexone or nalmefene. In some embodiments, the pharmaceutical formulation that is administered orally. In some embodiments, pharmaceutical formulation is administered sublingually. In some embodiments, the pharmaceutical formulation is administered as either a sustained release formulation, powder, solution, suspension, film, tablet, paste, oil, spray, pill or as a capsule. In some embodiments, the cannabinoid is cannabidiol and the partial opioid agonist is buprenorphine.

In some methods, the subject is administered from 2 mg to 900 mg of a cannabinoid compound. In some embodiments the subject is administered from 7 mg to 150 mg of a cannabinoid compound. In some embodiments the subject is administered from 30 mg to 150 mg of a cannabinoid compound. In some embodiments, the subject is administered 50 mg to 100 mg of a cannabinoid compound. In some embodiments the subject is administered from 100-200 mg of a cannabinoid. In some embodiments, the subject is administered 0.005 mg to 50 mg of a partial opioid agonist. In some embodiments, the subject is administered 0.05 mg to 50 mg of a partial opioid agonist. In some embodiments, the subject is administered 0.05 mg to 32 mg of a partial opioid agonist. In some embodiments, the subject is administered 0.01 mg to 1 mg of a partial opioid agonist. In an embodiment, the subject is administered 0.5 mg of buprenorphine. In some embodiments, the subject is administered 5 mcg to 1,000 mcg of buprenorphine. In some embodiments, the subject is administered 2-900 mg cannabidiol, 0.05-32 mg buprenorphine, and 0.1-15 mg naloxone. In some embodiments, the subject is administered 2-900 mg cannabidiol, 0.05-32 mg buprenorphine, and 0.1-8 mg naloxone. In some embodiments, the subject is administered 2-900 mg of cannabidiol and 5 mcg-32 mg of buprenorphine. In some embodiments, the buprenorphine is in a pharmaceutical formulation for sublingual or buccal administration. In some embodiments, the buprenorphine is in a pharmaceutical formulation for transdermal administration. In some embodiments, at least one cannabinoid compound is cannabidiol. In some embodiments of this method, the cannabidiol is in a pharmaceutical formulation for sublingual administration. In some embodiments of this method, the cannabidiol is in a pharmaceutical formulation for transdermal administration. In some embodiments, the cannabidiol and the buprenorphine are in the same pharmaceutical formulation. Other amounts of each of these compounds or a combination of these compounds are also provided later in the disclosure.

In some embodiments, a pharmaceutical formulation comprises cannabidiol and buprenorphine. In some embodiments, a pharmaceutical formulation consists essentially of cannabidiol and buprenorphine. In some embodiments, a pharmaceutical formulation comprises 2 mg to 900 mg of a cannabinoid and 5 mcg to 50 mg of a partial opioid agonist. In some embodiments, the pharmaceutical formulation comprises 0.005 mg to 32 mg of a partial opioid agonist. In some embodiments, the pharmaceutical formulation comprises 10 mg cannabidiol and 0.5 mg buprenorphine. In some embodiments, the pharmaceutical formulation comprises 30 mg cannabidiol and 0.5 mg buprenorphine. In some embodiments, the pharmaceutical formulation comprises 50 mg cannabidiol and 0.5 mg buprenorphine. In some embodiments, the formulation also comprises 0.1-8 mg naloxone or naltrexone. Other amounts of each of these compounds or a combination of these compounds are also provided later in the disclosure.

Some embodiments concern methods in which a purified cannabinoid compound and a partial opioid agonist are administered to the subject multiple times. In some embodiments, the least one purified cannabinoid and/or the partial opioid agonist are administered in a composition that is a pharmaceutical formulation. In some embodiments, at least one purified cannabinoid compound and the partial opioid agonist are administered multiple times over the course of at least 1 week. In some embodiments, at least one purified cannabinoid compound and a partial opioid agonist are administered multiple times over the course of at least 2 weeks.

Further aspects of the disclosure relate to a method of treating opioid use disorder, opioid withdrawal symptoms, and/or chronic pain in a subject comprising administering to the subject at least one purified cannabinoid compound and a partial opioid agonist wherein at least one purified cannabinoid and/or the partial opioid agonist are administered in a composition that is a pharmaceutical formulation. In some embodiments, the pharmaceutical formulation comprises cannabidiol and buprenorphine. In some embodiments, the pharmaceutical formulation comprises 2 mg to 900 mg of a cannabinoid and 5 mcg (0.005 mg) to 50 mg of a partial opioid agonist. In some embodiments, the formulation comprises 5 mcg (0.005 mg) to 32 mg of a partial opioid agonist. In some embodiments, the pharmaceutical formulation comprises 10 mg cannabidiol and 0.5 mg buprenorphine. In some embodiments, the pharmaceutical formulation comprises 30 mg cannabidiol and 0.5 mg buprenorphine. In some embodiments, the pharmaceutical formulation comprises 50 mg cannabidiol and 0.5 mg buprenorphine. In any and/or all of said embodiments, the pharmaceutical formulation further includes an opioid antagonist. In some embodiments, the opioid antagonist is naloxone, an oxymorphol analog of naloxone, a naloxone salt, a naloxone dehydrate, naltrexone or nalmefene. In some embodiments, the opioid antagonist is naloxone. In some embodiments, the opioid antagonist is naltrexone. Other amounts of each of these compounds or a combination of these compounds are also provided later in the disclosure.

Further aspects of the disclosure relate to a pharmaceutical composition comprising a cannabinoid and a partial opioid agonist. In some embodiments, the cannabinoid is a phytocannabinoid or a synthetic cannabinoid. In some embodiments, the phytocannabinoid is derived from a *Cannabis* plant. In some embodiments, the phytocannabinoid is derived from *Cannabis sativa*. In some embodiments, the cannabinoid is a purified compound. In some embodiments of the pharmaceutical composition, the cannabinoid is cannabidiol. In some and/or all embodiments of said pharmaceutical compositions, the partial opioid agonist is buprenorphine. In some embodiments, the pharmaceutical composition comprises 2 mg to 900 mg of a cannabinoid and 5 mcg (0.005 mg) to 50 mg of a partial opioid agonist. In some embodiments, the composition comprises 5 mcg (0.005 mg) to 32 mg of a partial opioid agonist. In some embodiments, the pharmaceutical composition comprises 10 mg cannabidiol and 0.5 mg buprenorphine. In some embodiments, the pharmaceutical composition comprises 30 mg cannabidiol and 0.5 mg buprenorphine. In some embodiments, the pharmaceutical composition comprises 50 mg cannabidiol and 0.5 mg buprenorphine. In any and/or all of said embodiments, the pharmaceutical composition further includes an opioid antagonist. In some embodiments, the opioid antagonist is naloxone, an oxymorphol analog of naloxone, a naloxone salt, a naloxone dehydrate, naltrexone or nalmefene. In some embodiments, the opioid antagonist is naloxone. In some embodiments, the partial opioid antagonist is naltrexone. In some embodiments the composition is formulated for oral administration. In some embodiments, the composition is formulated for sublingual or buccal administration. In some embodiments, the composition is formulated as a paste, oil, spray, pill, film, or capsule. In some embodiments, the composition is formulated for transdermal administration. In some embodiments, the pharmaceutical composition comprises 2 mg to 900 mg of a cannabinoid and 5 mcg (0.005 mg) to 50 mg of a partial opioid agonist. In some embodiments the composition comprises 10 mg to 200 mg of at least one purified cannabinoid compound. In some embodiments, the composition comprises 50 to 100 mg of the at least one purified cannabinoid compound. In some embodiments, the composition comprises 0.005 mg to 32 mg of a partial opioid agonist. In some embodiments, the composition comprises 0.1 mg to 10 mg of the partial opioid agonist. In some embodiments, the composition comprises 0.1 mg to 1 mg of the partial opioid agonist. Yet in further embodiments, the composition comprises 0.5 mg of buprenorphine. In some and/or all said pharmaceutical compositions, the composition comprises cannabidiol and buprenorphine. In some embodiments, the composition comprises 10 mg cannabidiol and 0.5 mg buprenorphine. In some embodiments, the composition comprises 30 mg cannabidiol and 0.5 mg buprenorphine. In other embodiments, the composition comprises 50 mg cannabidiol and 0.5 mg buprenorphine. In some and/or said pharmaceutical compositions, the composition further comprises naloxone. Other amounts of each of these compounds or a combination of these compounds are also provided later in the disclosure.

A further aspect of the disclosure relates to a pharmaceutical composition comprising 2-900 mg cannabidiol and 0.005-32 mg buprenorphine. Other amounts of each of these compounds or their combination are also provided later in the disclosure.

An additional aspect of the disclosure relates to a method of treating opioid use disorder, opioid withdrawal symptoms, and/or chronic pain in a subject comprising administering to the subject a pharmaceutical composition comprising 2-900 mg cannabidiol and 0.005-32 mg buprenorphine. In some embodiments of the method, the composition is administered orally or sublingually.

Yet a further aspect of the disclosure relates to a pharmaceutical composition comprising 2-900 mg cannabidiol, 0.005-32 mg buprenorphine, and 0.1-5 mg naloxone. Other amounts of each of these compounds or their combination are also provided later in the disclosure.

A further aspect of the disclosure relates to a method of treating opioid use disorder, opioid withdrawal symptoms, and/or chronic pain in a subject comprising administering to the subject a pharmaceutical composition comprising 2-900 mg cannabidiol, 0.005-32 mg buprenorphine, with or without 0.1-5 mg naloxone. Other amounts of each of these compounds or their combination are also provided later in the disclosure.

An additional aspect of the current disclosure relates to a method of treating opioid use disorder, opioid withdrawal symptoms, and/or chronic pain in a subject comprising administering to the subject the pharmaceutical composition comprising a purified cannabinoid and a partial opioid agonist in a ratio of 10:1, 20:1, 30:1, 40:1, 50:1, 60:1, 70:1, 80:1, 90:1 or 100:1, 200:1, 300:1, 400:1, 500:1, 600:1, 700:1, 800:1, 900:1, 1,000:1, 1,100:1, 1,200:1, 1,300:1, 1,400:1, 1,500:1, 1,600:1, 1,700:1, 1,800:1, 1,900:1, 2,000:1, 2,200:1, 2,400:1, 2,600:1, 2:800:1, 3,000:1, 3,200:1, 3,400:1, 3,600:1, 3,800:1, 4,000:1, 4,200:1, 4,400:1, 4,600:1, 4,800:1, 5,000:1, 5,200:1, 5,400:1, 5,600:1, 5:800:1, 6,000:1, 6,200:1, 6,400:1, 6,600:1, 6,800:1, 7,000:1, 7,200:1, 7,400:1, 7,600:1, 7,800:1, 8,000:1, 8,200:1, 8,400:1, 8,600:1, 8,800:1, 9,000:1, 9,200:1, 9,400:1, 9,600:1, 9,800:1, 10,000:1, 10,200:1, 10,400:1, 10,600:1, 10,800:1, 11000:1, 11,200:1, 11,400:1, 11,600:1, 11,800:1,12,000:1, 12,200:1, 12,400:1, 12,600:1, 12,800:1, 13,000:1, 13,200:1, 13,400:1, 14,000:1, 14,200:1, 14,400:1, 14,600:1, 14,800:1, 15,000:1, 15,200:1, 15,400:1, 15,600:1, 15,800:1, 16,000:1, 16,200:1, 16,400:1, 16,600:1, 16,800:1, 17,000:1, 17,200:1, 17,400:1, 17,600:1, 17,800:1, 18,000:1, 18,200:1, 19,000:1, 20,000:1, or any ratio in between. In some embodiments, the cannabinoid is cannabidiol. In some embodiments, the partial opioid agonist is buprenorphine.

Yet a further aspect of the current disclosure relates to a pharmaceutical composition comprising a purified cannabinoid and a partial opioid agonist in a ratio of 10:1, 20:1, 30:1, 40:1, 50:1, 60:1, 70:1, 80:1, 90:1 or 100:1, 200:1, 300:1, 400:1, 500:1, 600:1, 700:1, 800:1, 900:1, 1,000:1, 1,100:1, 1,200:1, 1,300:1, 1,400:1, 1,500:1, 1,600:1, 1,700:1, 1,800:1, 1,900:1, 2,000:1, 2,200:1, 2,400:1, 2,600:1, 2:800:1, 3,000:1, 3,200:1, 3,400:1, 3,600:1, 3,800:1, 4,000:1, 4,200:1, 4,400:1, 4,600:1, 4,800:1, 5,000:1, 5,200:1, 5,400:1, 5,600:1, 5:800:1, 6,000:1, 6,200:1, 6,400:1, 6,600:1, 6,800:1, 7,000:1, 7,200:1, 7,400:1, 7,600:1, 7,800:1, 8,000:1, 8,200:1, 8,400:1, 8,600:1, 8,800:1, 9,000:1, 9,200:1, 9,400:1, 9,600:1, 9,800:1, 10,000:1, 10,200:1, 10,400:1, 10,600:1, 10,800:1, 11000:1, 11,200:1, 11,400:1, 11,600:1, 11,800:1,12,000:1, 12,200:1, 12,400:1, 12,600:1, 12,800:1, 13,000:1, 13,200:1, 13,400:1, 13,600:1, 13,800:1, 14,000:1, 14,200:1, 14,400:1, 14,600:1, 14,800:1, 15,000:1, 15,200:1, 15,400:1, 15,600:1, 15,800:1, 16,000:1, 16,200:1, 16,400:1, 16,600:1, 16,800:1, 17,000:1, 17,200:1, 17,400:1, 17,600:1, 17,800:1, 18,000:1, 18,200:1, 19,000:1, 20,000:1, or any ratio in between. In some embodiments, the cannabinoid is cannabidiol. In some embodiments, the partial opioid agonist is buprenorphine. In some embodiments the pharmaceutical composition further comprises an opioid antagonist. In some embodiments, the opioid antagonist is naloxone, an oxymorphol analog of naloxone, a naloxone salt, a naloxone dehydrate, naltrexone or nalmefene. In some embodiments, the opioid antagonist is naloxone. In some embodiments, the oxymorphol analog of naloxone is naltrexone It is contemplated that any method or composition described herein can be implemented with respect to any other method or composition described herein and that different embodiments may be combined.

Use of the one or more compositions may be employed based on methods described herein. Use of one or more compositions may be employed in the preparation of medicaments for treatments according to the methods described herein. Other embodiments are discussed throughout this application. Any embodiment discussed with respect to one aspect of the disclosure applies to other aspects of the disclosure as well and vice versa. The embodiments in the Example section are understood to be embodiments that are applicable to all aspects of the technology described herein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4 illustrates a Study Schema in accordance with the current invention.

DETAILED DESCRIPTION OF ILLUSTRATIVE EMBODIMENTS

Figure 1:
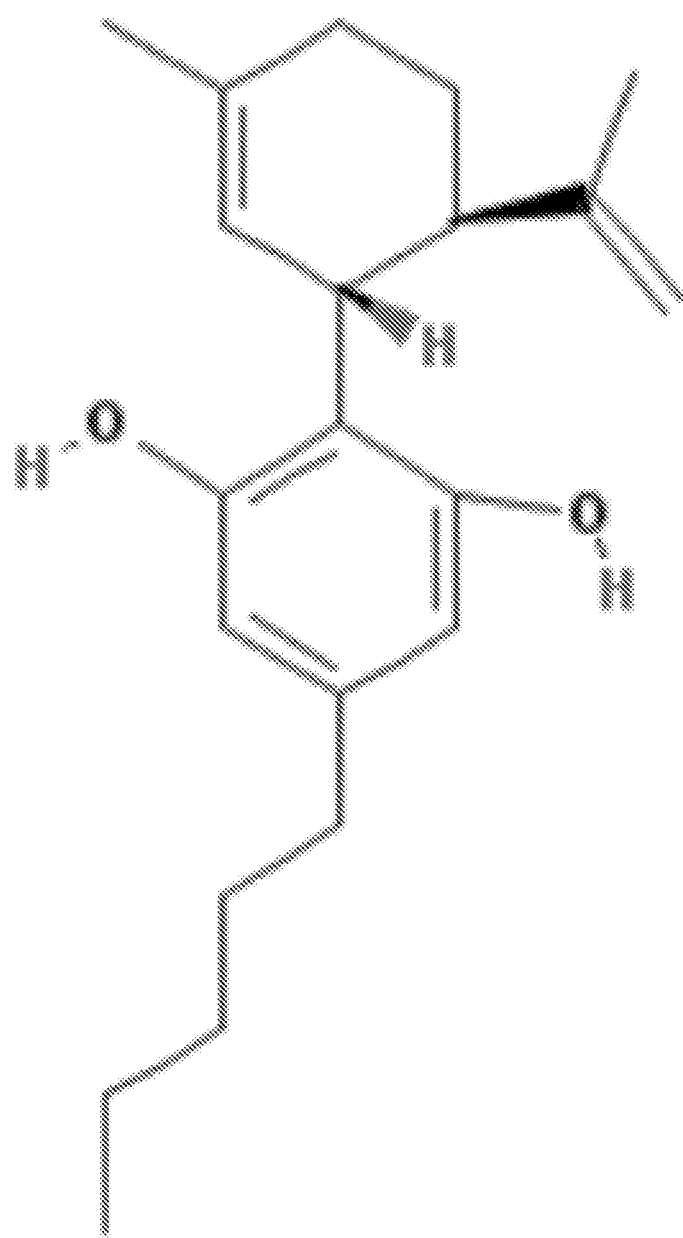
FIG. 1 depicts the 2D chemical structure of cannabidiol.

Opioid analgesics are significantly limited by serious side effects including tolerance, dependence, and risk of overdose and addiction. Safer analgesic alternatives to current opioid analgesics are needed. Despite the availability of some therapeutic compositions, an effective treatment for opioid use disorder, opioid withdrawal symptoms and/or chronic pain is lacking catapulting these conditions to an increasingly serious and challenging public health issue. The current methods and compositions provide for novel and safe therapeutic approaches for treating opioid use disorder, opioid withdrawal symptoms and/or chronic pain. The inventors discovered synergistic analgesic and opioid sparing effects of the combination of low dose buprenorphine and cannabidiol.

According to certain aspects of the disclosure, a method for treating opioid use disorder, opioid withdrawal symptoms and/or chronic pain in a subject, comprises administering to the subject at least one purified cannabinoid compound and a partial opioid agonist. In some embodiments, the purified cannabinoid compound and the partial opioid agonist are administered within hours (such as 24 hours for example) from each other. In some embodiments, the purified cannabinoid compound and the partial opioid agonist are administered at the same time. In some embodiments the purified cannabinoid is cannabidiol. In some embodiments, the partial opioid agonist is buprenorphine. In some embodiments, the methods further include an opioid antagonist, such as for example naloxone. Yet, in other embodiments, the method comprises administering a pharmaceutical formulation or a composition comprising purified cannabidiol (CBD) and buprenorphine. In some embodiments, the method comprises administering a pharmaceutical formulation or a composition comprising purified cannabidiol (CBD) and buprenorphine and an opioid antagonist such as, for example, naloxone.

According to other aspects of the disclosure pharmaceutical compositions comprising at least one purified cannabinoid compound and a partial opioid agonist are provided. In some embodiments, the purified cannabinoid compound and the partial opioid agonist are administered within hours (such as 24 hours for example) from each other. In some embodiments, the purified cannabinoid compound and the partial opioid agonist are administered at the same time. In some embodiments the purified cannabinoid is cannabidiol. In some embodiments, the partial opioid agonist is buprenorphine. In some embodiments, the methods further include an opioid antagonist, such as for example naloxone. Yet, in other embodiments, the composition is a pharmaceutical formulation comprising purified cannabidiol (CBD) and buprenorphine. In some embodiments, the pharmaceutical formulation or composition comprises purified cannabidiol (CBD) and buprenorphine and an opioid antagonist such as, for example, naloxone.

The current disclosure teaches that the combination of a purified cannabinoid with a partial opioid agonist has the potential to be more effective and safer than either compound alone. The combination of cannabidiol and buprenorphine, as way of example, works in synergy to enhance the anxiolytic effects of CBD and/or the analgesic and anti-opioid craving/withdrawal effects of buprenorphine such that the combination of cannabidiol and buprenorphine produces synergistic effects where the effect with the combination is more than additive. Furthermore, both CBD and buprenorphine are metabolized by Cytochrome P450 3A4 (CYP 3A4) enzymes and CBD also inhibits CYP 3A4 in an in vitro study. (Stout and Cimino 2014) Concomitant administration of CBD and buprenorphine may reduce buprenorphine metabolism thereby achieving analgesic effects with lower doses of buprenorphine.

Reductions in anxiety may reduce opioid relapse during buprenorphine maintenance treatment and opioid detoxification with buprenorphine. Reductions in anxiety and pain catastrophizing may reduce opioid doses and opioid abuse and reduce pain intensity and pain interference in patients treated with buprenorphine for chronic pain. Reductions in anxiety comorbid with opioid use, opioid withdrawal, and/or chronic pain may significantly reduce opioid overdose rates by reducing use of opioids with more dangerous anxiolytic sedatives including benzodiazepines. Unlike benzodiazepines, other sedative-hypnotics, and muscle relaxants, CBD did not reduce respiratory rate in rats (Graham ad Li, 1973). A combination sublingual formulation may improve treatment adherence compared to use of the individual formulations especially with current non-approved "medical marijuana" formulations of CBD that are currently available.

The texts of the references cited in this disclosure are herein incorporated by reference in their entireties. The meaning of terms as intended is defined herein below.

I. Definitions

"Opioid Use Disorder" refers to a condition characterized by the harmful consequences of repeated opioid use, a pattern of compulsive opioid use, and sometimes physiological dependence on opioid including tolerance and/or symptoms of withdrawal.

"Drug withdrawal" refers to a group of symptoms that occur upon the abrupt discontinuation or sudden decrease in intake of medications or recreational drugs. Consequently, "opioid withdrawal" refers to the group of symptoms that occur upon the dramatic reduction, abrupt discontinuation or decrease in intake of opioids or opiates. Withdrawal symptoms may also start between doses. Withdrawal symptoms from opioids include but are not limited to anxiety, depression, sweating, vomiting, and diarrhea, muscle cramping, agitation, insomnia, yawning dilated pupils, goose bumps, abdominal cramping, runny nose and increased tearing, for example.

"Chronic pain" refers to pain that lasts for extended periods of time, sometimes weeks or even months The term "cannabinoid" refers to any compound derived from the *Cannabis* plant or a pharmaceutically acceptable salt, solvate, metabolite, metabolic precursor, derivative, analogue or synthetic version of a compound derived from the *Cannabis* plant and various cannabinoid mimetics including their pharmaceutically acceptable salts, solvates, metabolites, metabolic precursors and derivatives thereof.

The term "cannabidiol" refers to cannabidiol; cannabidiol prodrugs; a pharmaceutically acceptable derivatives of cannabidiol, including pharmaceutically acceptable salts of cannabidiol, cannabidiol prodrugs, cannabidiol solvates, cannabidiol metabolites, cannabidiol metaboic precursors, cannabidiol derivatives and homologs.

"A purified cannabinoid compound" is defined as a compound containing cannabinoid that have been extracted from the *cannabis* plant and purified to the extent that other cannabinoids and non-cannabinoid components that are co-extracted with the cannabinoids have been substantially removed.

The term "substantially the same" or "not significantly different" refers to a level of expression that is not significantly different than what it is compared to. Alternatively, or in conjunction, the term substantially the same refers to a level of expression that is less than 2, 1.5, or 1.25 fold different than the expression or activity level it is compared to.

A "subject," "individual" or "patient" is used interchangeably herein and refers to a vertebrate, for example a primate, a mammal or a human. Mammals include, but are not limited to equines, canines, bovines, ovines, murines, rats, simians, humans, farm animals, sport animals and pets. Also intended to be included as a subject are any subjects involved in clinical research trials not showing any clinical sign of disease, or subjects involved in epidemiological studies, or subjects used as controls.

"Diagnosis" may refer to the process of attempting to determine or identify a possible disease or disorder, or to the opinion reached by this process. From the point of view of statistics the diagnostic procedure may involve classification tests.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. In some embodiments it is contemplated that a numerical value discussed herein may be used with the term "about" or "approximately." The term "about" or "around" is also used to indicate that a value includes the standard deviation of error for the device or method being employed to determine the value.

As used herein, the term "comprising" is intended to mean that the compositions and methods include the recited elements, but not excluding others. "Consisting essentially of" when used to define compositions and methods, shall mean excluding other elements of any essential significance to the combination for the stated purpose. "Consisting essentially of" in the context of pharmaceutical compositions of the disclosure is intended to include all the recited active agents and excludes any additional non-recited active agents, but does not exclude other components of the composition that are not active ingredients. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention. It is contemplated that embodiments described in the context of the term "comprising" may also be implemented in to context of the term "consisting of" or "consisting essentially of."

The terms "protein", "polypeptide" and "peptide" are used interchangeably herein when referring to a gene product or functional protein.

The terms "ameliorating," "inhibiting," or "reducing," or any variation of these terms, when used in the claims and/or the specification includes any measurable decrease or complete inhibition to achieve a desired result.

The term "inhibitor" refers to a therapeutic agent that indirectly or directly inhibits the activity or expression of a protein, process (e.g. metabolic process), or biochemical pathway The term "agonist" describes a moiety or agent that interacts with and activates a receptor such as a G-protein-coupled receptor, for instance an opioid receptor, and can thereby initiate a physiological or pharmacological response characteristic of that receptor.

As used herein, a "partial agonist" is moiety, or agent, that binds to and activates a given receptor, but have only partial efficacy at the receptor relative to a full agonist.

As used herein an "antagonist" describes a moiety that competitively binds to the receptor at the same site as an agonist, but does not activate the intracellular response initiated by the active form of the receptor and can thereby inhibit the intracellular responses by an agonist or partial agonist.

The term "pharmaceutical formulation" is intended to mean a composition or a mixture of compositions comprising at least one active ingredient; including but not limited to, salts, solvates, and hydrates of compounds described herein.

As used herein, "treating," "treatment" or "therapy" is an approach for obtaining beneficial or desired clinical results. This includes the reduction or the alleviation of symptoms, the reduction or alleviation of pain, or the reduction in the frequency of withdrawal symptoms, and/or reduction in the occurrence of anxiety or depression and/or reduction in suicidal thinking. Furthermore, these terms are intended to encompass curing as well as ameliorating at least one symptom of the condition or disease. For example, in the case of opioid use disorders, a response to treatment includes the cessation in the use of opioids, or the cessation of at least one opioid withdrawal symptom.

The term "therapeutically effective amount" refers to an amount of the drug that treats or inhibits chronic pain, opioid use disorder or opioid withdrawal symptoms in the subject. In some embodiments, the therapeutically effective amount inhibits at least or at most or exactly 100, 99, 98, 96, 94, 92, 90, 85, 80, 75, 70, 65, 60, 55, 50, 40, 30, 20, or 10%, or any derivable range therein, of a symptom expression.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Furthermore, an embodiment discussed in the Examples may be applied in the context of any other embodiments discussed herein.

The use of the word "a" or "an" when used in conjunction with the term "comprising" in the claims and/or the specification may mean "one," but it is also consistent with the meaning of "one or more," "at least one," and "one or more than one."

II. Opioid Use Disorder, Opioid Withdrawal, and Chronic Pain

Opioids include most prescription analgesics as well as products of the poppy plant (e.g., opium, morphine, heroin, Oxycontin, Dilaudid, methadone, codeine and others). Opioids are conventionally prescribed to control pain, reduce cough, or relieve diarrhea, they also produce feelings of sedation, tranquility, and euphoria, that may lead the patient to continue to take these drugs despite the development of serious related problems. These problems include the need to escalate doses in order to achieve these desired effects. Escalated levels of opioids can overwhelm respiratory drive and lead to death.

Opioid Use Disorder is a condition characterized by the harmful consequences of repeated opioid use, a pattern of compulsive opioid use, and sometimes physiological dependence on opioid such as tolerance and/or symptoms of withdrawal. Withdrawal symptoms can be produced just hours after the last dose, and the symptoms can last for a week or more. Characteristic symptoms of withdrawal include but are not limited to anxiety, agitation, fatigue, irritability, shaking, muscle aches, sweating, insomnia, increased tearing, runny nose, yawning and depression. Additional late symptoms of withdrawal may include abdominal cramping, diarrhea, dilated pupils, goose bumps, nausea and vomiting. Though withdrawal symptoms can be very uncomfortable and unsettling, and somehow dangerous if done without professional care, they are not life-threatening. The biggest complication is patient's returning to drug use. Unassisted withdrawal can lead to relapse. It is reported that most opiate overdose deaths occur in people who have just detoxed. Withdrawal reduces the person's tolerance to the drug, so those who have just gone through withdrawal can overdose on a much smaller dose than they used to take.

Several drugs are conventionally used for the treatment of withdrawal symptoms including methadone. Methadone relieves withdrawal symptoms and helps with detoxification. It can be used as a long-term maintenance medicine for opioid dependence. After a period of maintenance, the dose may be decreased slowly over a long time. This helps reduce the intensity of withdrawal symptoms. Some people stay on methadone for years.

Another drug commonly used to treat opioid withdrawal is buprenorphine which usually shortens the length of the detoxification period. Buprenorphine may also be used for long-term maintenance. It can be combined with naloxone, for example, so as to help prevent dependence and misuse. Buprenorphine may also be used with Naltrexone to help prevent relapse. Another drug that can be used in patients suffering from opioid withdrawal is clonidine, which although does not help reduce cravings, it does help with anxiety, agitation, seating, runny nose, muscle aches and abdominal cramping.

Chronic pain is often used to refer to pain that last for extended periods of time, sometimes weeks or even months. Some authors consider ongoing pain lasting longer than 6 months as diagnostic, while others have used 3 months or 12 weeks as a minimum criterion for diagnosis. Chronic pain may arise from an injury or continued illness for example. Chronic pain may limit a person's movements, which can reduce flexibility, strength, and stamina. This difficulty in carrying out important and enjoyable activities can lead to disability and despair. Anxiety is frequently co-morbid with chronic pain conditions and is a common trigger for opioid use and relapse among patients with opioid use disorders, opioid withdrawal, and chronic pain. Pain catastrophizing is also associated with higher risk of prescription opioid abuse as well as worse clinical outcomes for pain management. Chronic pain syndrome is a common problem that presents a major challenge to health-care providers because of its complex natural history, unclear etiology, poor response to therapy and its poorly defined and personal nature.

III. THERAPEUTIC AGENTS

A. Cannabinoids/Cannabidiol

Cannabidiol (CBD) is a compound found in the *Cannabis* genus of plants. *Cannabis sativa* contains more than 500 identified phytochemicals, with at least 104 being cannabinoids (phytocannabinoids). The major psychoactive compound found in *cannabis* is 49-tetrahydrocannabinol ($\Delta 9$-THC). $\Delta 9$-THC mimics endogenous cannabinoid neurotransmitters (endocannabinoids) by binding to two cell membrane receptors: cannabinoid type 1 (CB1) and cannabinoid type 2 (CB2)—found in immune and hematopoietic cells. $\Delta 9$-THC is thought to be responsible for many of the potential negative consequences of *cannabis* use including addiction, psychosis, cognitive impairment, weight gain, anhedonia, and rebound anxiety and insomnia. In contrast, CBD does not bind CB1 or CB2 receptors and does not have psychoactive or addictive properties and has been purported to be responsible for many of the "medicinal" properties of *cannabis*. In particular, CBD has anti-anxiety properties as a 5-HT1A partial agonist and is being investigated as a potential anxiolytic. A variety of medical marijuana formulations purporting to contain CBD extracts are available from medical marijuana dispensaries but no CBD formulation is FDA-approved for any indication and the quality and reliability of CBD formulations from medical marijuana dispensaries and distributors is uncertain. Use of "medical marijuana" has exploded but is not FDA-approved for any indication, quality control for medicinal marijuana products varies greatly, and there is little ability for patients and physicians to accurately dose these medications. Further, medical marijuana containing $\Delta 9$-THC and CBD exposes patients to the risks of $\Delta 9$-THC use.

More than 27 million Americans use some form of marijuana each month. Legal *cannabis* sales in the US reached an estimated $1.7 billion nationwide. Estimates put California's medicinal use around 750,000 patients or 19.4 per 1000 population. The market for *cannabis* products is likely to explode as states loosen legal restrictions on marijuana use, although none of these formulations are FDA-approved and access to medical marijuana products is currently limited to the 28 US states that have legalized some form of medicinal marijuana use.

Cannabinoids are a group of extracellular signaling molecules that are found in both plants and animals. Signals from these molecules are mediated in animals by two G-protein coupled receptors, Cannnabinoid Receptor 1 (CB1) and Cannabinoid Receptor 2 (CB2). CB1 is expressed most abundantly in the neurons of the CNS (in brain basal ganglia, cerebellum, hippocampus, neocortex, and hypothalamus) and in some peripheral tissues and cells. CB2 is expressed predominantly in non-neural tissues, such as for example in immune and hematopoietic cells as well as in, endothelial cells, osteoblasts, osteoclasts, the endocrine pancreas, and cancerous cell lines. As such, CB1 is believed to be primarily responsible for mediating the psychotropic effects of cannabinoids on the body, whereas CB2 is believed to be primarily responsible for most of their non-neural effects.

Cannabinoids according to the present disclosure include pharmaceutically acceptable salts, solvates, metabolites, metabolic precursors, and derivatives of cannabinoids. This also encompasses analogs of cannabinoids such as tetrahydropyran analogs, including, for example, delta-9-tetrahydrocannabinol, delta-8-tetrahydrocannabinol, 6,6,9-trimethyl-3-pentyl-6H-dibenzo[b,d]pyran-1-ol, 3-(1,1-dimethylheptyl)-6,6a,7,8,10,10a-hexahydro-1-hydroxy-6,6-dimethyl-9H-dibenzo[b,d]pyran-9-one, (−)-(3S,4S)-7-hydroxy-delta-6-tetrahydrocannabinol-1,1-dimethylheptyl, (+)-(3S,4S)-7-hydroxy-delta-6-tetrahydrocannabinol-1,1-dimethylheptyl, 1 1-hydroxy-delta-9-tetrahydrocannabinol, and delta-8-tetrahydrocannabinol-11-oic acid)); certain piperidine analogs (e.g., (−)-(6S,6aR,9R,10aR)-5,6,6a,7,8,9,10,10a-octahydro-6-methy-1-3-[(R)-1-methyl-4-phenylbutoxy]-1,9-phenanthridinediol 1-acetate)), certain aminoalkylindole analogs (e.g., (R)-(+)-[2,3-dihydro-5-methyl-3-(4-morpholinylmethyl)-pyrrolo [1,2,3-de]-1,4-benzoxazin-6-yl]-1-naphthalenyl-methanone), certain open pyran-ring analogs (e.g., 2-[3-methyl-6-(1-methylethenyl)-2-cyclohexen-1-yl]-5-pentyl-1,3-benzenedi-ol and 4-(1,1-dimethylheptyl)-2,3'-dihydroxy-6'alpha-(3-hydroxypropyl)-r, -2',3',4',5',6'-hexahydrobiphenyl).

Cannabinoids including cannabidiol are compounds found in the *Cannabis* plant. *Cannabis sativa* contains more than 500 identified phytochemicals, with at least 104 being cannabinoids (phytocannabinoids). The major psychoactive compound found in *Cannabis* is Δ9-tetrahydrocannabinol (Δ9-THC). Δ9-THC mimics endogenous cannabinoid neurotransmitters (endocannabinoids) by binding to two cell membrane receptors: cannabinoid type 1 (CB1)—found primarily in brain (basal ganglia, cerebellum, hippocampus, neocortex, and hypothalamus) and some peripheral tissue and cannabinoid type 2 (CB2)—found in immune and hematopoietic cells. Δ9-THC is thought to be responsible for many of the potential negative consequences of *cannabis* use including addiction, psychosis, cognitive impairment, weight gain, anhedonia, and rebound anxiety and insomnia. Another compound found in *Cannabis* is cannabidiol (CBD). The molecular formula for CBD is C21H3002 and its structure is depicted in FIG. 1. In contrast to Δ9-THC, CBD does not bind CB1 or CB2 receptors and does not have psychoactive or addictive properties and has been purported to be responsible for many of the "medicinal" properties of *cannabis*. In particular, CBD has anti-anxiety properties as a 5-HT1A (5-hydroxytryptamine receptor) partial agonist and is being investigated as a potential anxiolytic. A variety of medical marijuana formulations purporting to contain CBD extracts are available from medical marijuana dispensaries but no CBD formulation is FDA-approved for any indication and the quality and reliability of CBD formulations from medical marijuana dispensaries and distributors is uncertain. Use of "medical marijuana" has exploded but is not FDA-approved for any indication, quality control for medicinal marijuana products varies greatly, and there is little ability for patients and physicians to accurately dose these medications. Further, medical marijuana containing Δ9-THC and CBD exposes patients to the risks of Δ9-THC use.

A cannabidiol, according to the current disclosure includes cannabidiol (CBD), pharmaceutically acceptable derivatives of cannabidiol, pharmaceutically acceptable salts of cannabidiol, cannabidiol prodrugs, cannabidiol solvates, cannabidiol metabolites, cannabidiol metaboic precursors, cannabidiol derivatives and cannabidiol homologues such as, for example, cannabidivarin. Cannabidiol may be in any suitable form for administration to a mammal such as in the form of a free base, free acid, salt, hydrate, anhydrate, enantiomer, isomer, tautomer, polymorph, or the like, provided that the free base, salt, hydrate, enantiomer, isomer, tautomer, or polymorph is therapeutically active or undergoes conversion within or outside of the body to a therapeutically active form of cannabidiol.

The cannabinoid compositions of the present disclosure, including cannabidiol can be derived from various sources. Sources can be natural, naturally-derived or synthetic. For example, the cannabinoid, or mixture of cannabinoids, can be obtained or purified from the extract from of a natural source, such as plants from the *cannabis* genus (e.g., *Cannabis sativa*, *Cannabis indica* and *Cannabis ruderalis*). In an alternative embodiment, the cannabinoids also encompass highly purified, Pharmacopoeial Grade substances, obtained via synthetic chemical reactions.

B. Partial Opioid Agonists

Opioids produce both analgesia and euphoria. The mood altering action of opioids in addition to the physical dependence and addictive qualities of this class of drugs encourages abuse. Opioid agonists are known in the art and include but are not restricted to, alfentanil, allylprodine, alphaprodine, anileridine, benzylmorphine, bezitramide, brifentanil, carfentanil, clonitazene, codeine, dextromoramide, desomorphine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, fentanyl, heroin, hydrocodone, hydromorphone, hydroxypethidine, isomethadone, ketobemidone, levorphanol, levallorphan, levomethadone, levophenacylmorphan, lofentanil, meperidine (pethidine), metazocine, methadone, metopon, 4-methoxymethylfentanyl, 3-methylfentanil, mirfentanil, 6-monoacetylmorphine, morphine, morphine-6-glucuronide, ohmefentanyl, oxycodone, oxymorphone, propoxyphene, pentazocine, propiram, propoxyphene, racemorphan, sufentanil, tapentadol, tramadol and tilidine. Other examples of partial opioid agonists include nalorphine, lofexidine butorphanol, dezocine and nalbulphine.

In embodiments of the methods and compositions provided and described herein, the partial opioid agonists may be, but is not restricted to buprenorphine (BUP), the international non-proprietary name for which is: (N-cyclopropylmethyl-7.alpha.-[1-(S)-hydroxy-1,2,2-trimethylpropyl]6, 14-end oethano-6,7,8,14-tetrahydronororipavine). Buprenorphine is a μ-opioid partial agonist which produces typical μ-opioid agonist effects and side effects such as additive potential and respiratory depression while producing maximal effects that are less than those of full agonists like heroin and methadone. At low doses buprenorphine produces sufficient μ-agonist effect to enable opioid-addicted individuals to discontinue the misuse of opioids without experiencing withdrawal symptoms. It is within the knowledge of a person of skill in the art that other partial opioid agonists may be used without departing from the scope of the current disclosure. In some embodiments, the compositions and methods for treating opioid use disorder, opioid withdrawal symptoms or chronic pain comprises other partial opioid agonists, such as by way of example, mitragynine, 7 hydroxymitragynine derived from the plant *Mitragyna speciosa* (commonly known as kratom), and pharmaceutically acceptable derivatives of mitragynine, pharmaceutically acceptable salts of mitragynine, mitragynine prodrugs, mitragynine solvates, mitragynine metabolites, mitragynine metaboic precursors, and mitragynine derivatives, such as 9-OH corynantheidine.

Figure 2:
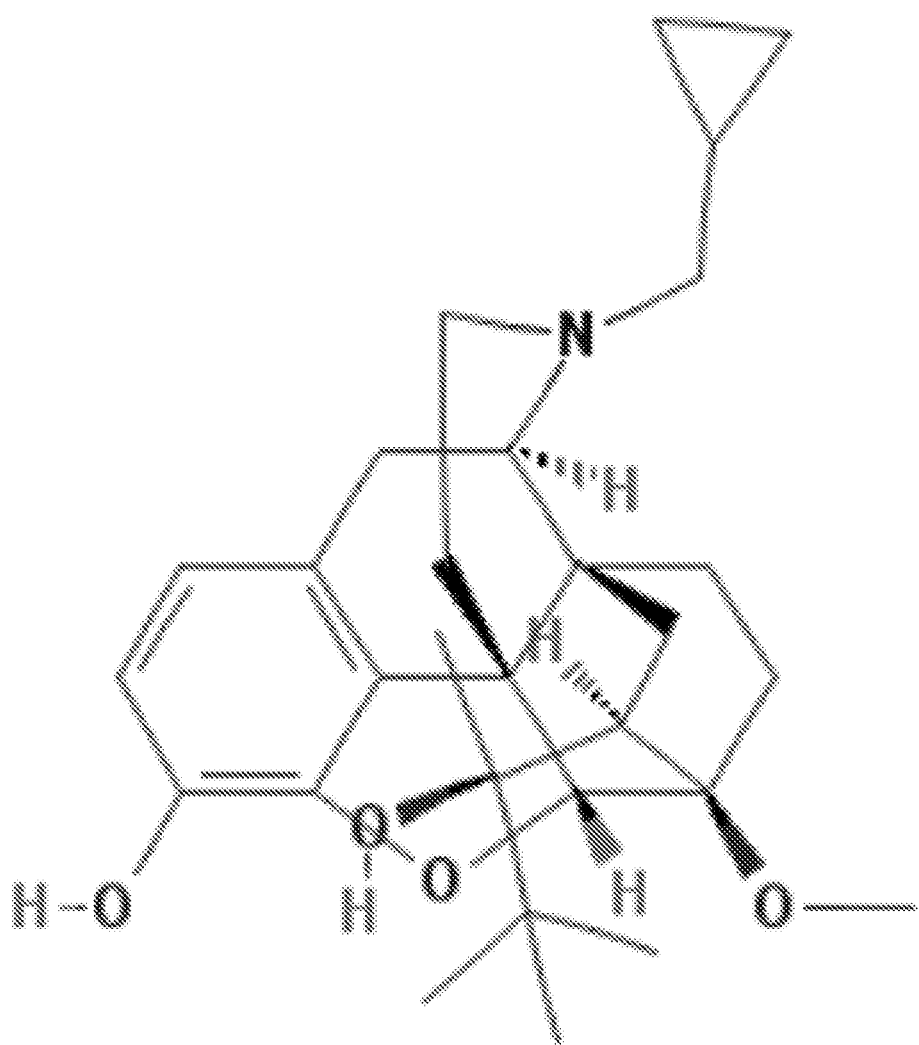
FIG. 2 depicts the 2D chemical structure of buprenorphine.
Figure 3:
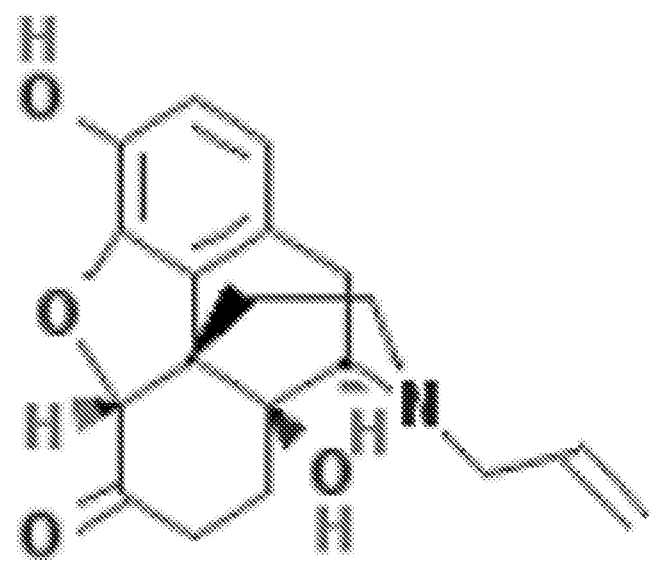
FIG. 3 illustrates the chemical structure of buprenorphine and naloxone.
Figure 3:
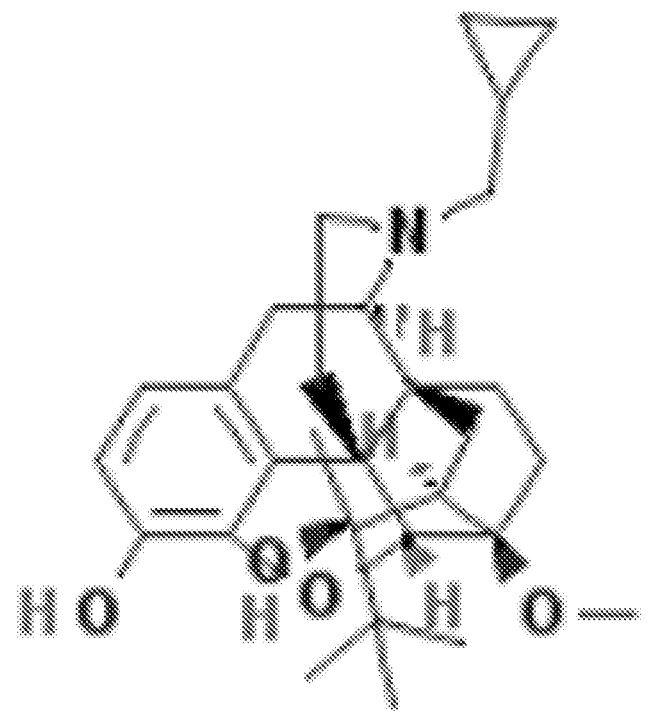

BUP in combination with naloxone are currently FDA-approved in a variety of formulations for sublingual, transdermal and/or buccal administration for the treatment of opioid use disorder, opioid withdrawal, and chronic pain. The molecular formula for buprenorphine is $C_{29}H_{41}NO_4$ and its structure is depicted in FIG. 2. The molecular formula for buprenorphine and naloxone is $C_{48}H_{62}N_2O_8$ and its structure is depicted in FIG. 3. Naloxone is included with the aim of deterring abuse of buprenorphine via the intravenous route. Buprenorphine has a lower risk of overdose compared to full opioid agonists (e.g. morphine, hydrocodone, methadone, oxycodone) due to a "ceiling effect" on respiratory depression due to buprenorphine's activity as a partial opioid agonist. Opioids including buprenorphine are frequently prescribed with dangerous sedatives and anxiolytics including benzodiazepines and patients frequently abuse alcohol with opioids. Overdose due to opioids with sedatives including benzodiazepines play an important role in the current epidemic of opioid overdose deaths.

C. Opioid Antagonists/Ligands

In some embodiments, partial opioid agonists can be prepared with other compounds. For example, preparations have been developed which protect the oral preparations of certain opioids from parenteral abuse by the incorporation of the narcotic analgesic naloxone (naloxone, chemically known as 1-N-allyl-14-hydroxynordihydromorphinone). These preparations are based on the low oral bio-availability (about 0.1%) of naloxone when compared to that of the opioids. Thus an amount of naloxone can be introduced into oral preparations of these analgesics that is sufficient to prover aversive to a narcotic addict by parenteral administration whereby such amount is not sufficient to compromise the analgesic effect of the opioids. If the opioid-naloxone preparations are dissolved in water and injected the naloxone is active and shows its narcotic antagonist activity. It thus blocks the euphorigenic activity of the opioid and eliminates the development of psychological dependence. The inhibition of opiate effects by naloxone also prevents the development of physical dependence. U.S. Pat. No. 3,773,955 to Pachter and Gordon, incorporated herein by reference, describes the oral combination of naloxone with a number of opiates particularly methadone. U.S. Pat. No. 4,457,933 to Pachter and Gordon describes the protection with naloxone of oral dosage forms of various opioids against both oral and parenteral abuse. U.S. Pat. No. 4,661,492 mentions the incorporation of 1-3 mg of naloxone in an oral unit dose of buprenorphine (2 mg)

In some embodiments, the compositions include an oxymorphol analog of naloxone, a naloxone salt, or a naloxone dihydrate.

Other preparations of buprenorphine combines it with naltrexone (1-N-cyclopropylmethyl-14-hydroxynordihydromorphinone). Naltrexone is a pure opiate antagonist which, when administered orally as a maintenance drug for opiate addicts, blocks the effects of self-administered opiates thereby contributing to the extinction of drug craving. A limited range of ratios of buprenorphine with naltrexone for which, by injection, the analgesic performance is equal to that of buprenorphine alone whilst the abstinence-precipitating effects in opiate-dependent subjects are equivalent to that of naltrexone alone.

In some embodiments, nalmefene (also known as nalmetrene), another opioid antagonist can be used in combination with the compositions described herein. Nalmefene is similar in both structure and activity to naltrexone. Reported advantages of nalmefene relative to naltrexone include longer half-life, greater oral bioavailability and no observed dose-dependent liver toxicity. As with other opioid antagonists of the sort, nalmefene may precipitate acute withdrawal symptoms in patients who are dependent on opioid drugs, or post-operatively, to counteract the effects of strong opioids used in surgery. Any other opioid antagonist that can potentiate or enhance the effectiveness of a partial opioid agonist is contemplated and within the scope of the current invention.

IV. Formulations, Dosage Abd Routes of Administration

Embodiments include pharmaceutical, therapeutic compositions, formulations, preparations and related methods for treating opioid use disorders, opioid withdrawal symptoms and/or chronic pain. Administration of the compositions will typically be via sublingual, buccal or transdermal routes.

Compositions take the form of a solution, suspension, film, paste, sustained release formulation or powder for example, and contain about 10% to about 95% of active ingredient, or about 25% to about 70%. In embodiments, the compositions are administered sublingually and/or via the buccal mucosa or transdermally.

Compositions are administered in a manner compatible with the dosage formulation, and in such amount as will be therapeutically effective, tolerable and safe. The quantity administered depends on the subject to be treated. Precise amounts of active ingredient required to be administered depend on the judgment of the practitioner.

In many instances, it may be desirable to have multiple administrations of at most about or at least about 3, 4, 5, 6, 7, 8, 9, 10, or more (or any range derivable therein). The administration may range from 2 day to multiple week interval of 1, 2, 3, 4, 5, 6, 7, 8, 9, 10 or more weeks (or any range derivable therein). The course of administration may be followed by assessment of symptoms, pain, mood, behavior, catastrophizing for example.

A. Dosage

The dosage of the pharmaceutical compositions and formulations depends on the type of formulation and varies according to the size and health of the subject. Various combination and dosages are contemplated and are within the scope of the current invention and within the scope of "pharmaceutically acceptable" or "pharmacologically acceptable" compositions, such as, by way of example, any dosage anywhere between 2-900 mg for cannabidiol and 0.005-32 mg for buprenorphine with or without naloxone at a 4:1 ratio, for example 2 mg buprenorphine/0.5 mg naloxone. The phrases "pharmaceutically acceptable" or "pharmacologically acceptable" refer to molecular entities and compositions that do not produce an adverse, allergic, or other untoward reaction when administered to an animal, or human.

The optimal doses of CBD and buprenorphine for sublingual administration in a combination sublingual formulation is not obvious due to complex pharmacokinetics and pharmacodynamics of both CBD and buprenorphine. Combining CBD with BUP is a novel approach that will achieve improvements in pain and pain-related negative affect with ultra-low doses of buprenorphine.

Upon formulation, solutions will be administered in a manner compatible with the dosage formulation and in such amount as is therapeutically or prophylactically effective. The formulations are easily administered in a variety of dosage forms, such as the oral formulations described above. An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

In certain embodiments, a subject is administered cannabidiol or cannabidivarin in an amount of about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or µg/kg or micrograms/kg/minute or mg/kg/min or micrograms/kg/hour or mg/kg/hour, or any range derivable therein.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of a condition. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of the condition (or any range derivable therein). The patient may be treated for 1, 2, 3, 4, 5, 6, 7, 8, 9, 10 or more days (or any range derivable therein) or until symptoms of the condition have disappeared or been reduced or after 6, 12, 18, or 24 hours or 1, 2, 3, 4, or 5 days after symptoms have disappeared or been reduced.

In some embodiments, treatments of subjects may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

A patient may be administered a composition or a combination of compounds described herein in an amount that is, is at least, or is at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg (or any range derivable therein).

A patient may be administered a composition or a combination of compounds described herein in an amount that is, is at least, or is at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg/kg/day (or any range derivable therein).

B. Cannabinoids/Cannabidiol

Bioavailability of cannabidiol (CBD) after oral administration is reported to be 13-19%. CBD undergoes extensive first-pass metabolism (Pisanti et al. 2017). Bioavailability of sublingual CBD is not well characterized but would be expected to be higher than for oral dosing as sublingual administration would bypass first-pass metabolism after oral dosing. Preclinical studies as well as sparse clinical data suggest a possible inverted-U dose response curve for CBD's anxiolytic effect but have not identified the optimal dose. Several human studies have variably identified oral doses between 300 mg and 600 mg as having optimal effects after acute dosing (Crippa et al. 2004; Crippa et al. 2011; Zuardi et al. 2017).

In one embodiment, compositions disclosed herein comprise cannabinoids, or cannabidiol a cannabidiol precursor or analogue or homolog in a total amount by weight of the composition of about 0.1% to about 95%. For example, the amount of cannabidiol by weight of the composition may be about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.1%, about 5.2%, about 5.3%, about 5.4%, about 5.5%, about 5.6%, about 5.7%, about 5.8%, about 5.9%, about 6%, about 6.1%, about 6.2%, about 6.3%, about 6.4%, about 6.5%, about 6.6%, about 6.7%, about 6.8%, about 6.9%, about 7%, about 7.1%, about 7.2%, about 7.3%, about 7.4%, about 7.5%, about 7.6%, about 7.7%, about 7.8%, about 7.9%, about 8%, about 8.1%, about 8.2%, about 8.3%, about 8.4%, about 8.5%, about 8.6%, about 8.7%, about 8.8%, about 8.9%, about 9%, about 9.1%, about 9.2%, about 9.3%, about 9.4%, about 9.5%, about 9.6%, about 9.7%, about 9.8%, about 9.9%, about 10%, about 11%, about 12%, about 13% about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90% or about 95% or any amount deliverable in between.

The compositions disclosed herein are used in pharmaceutical formulations and in pharmacologically effective amounts. In an embodiment, the amount of pharmaceutical composition administered is set to deliver a therapeutically effective amount of the cannabinoid, cannabidiol, a cannabidiol homologue, a cannabidiol derivatives, cannabidivarin and/or a 5-HT1A partial agonist that is, at least, or is at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100, 101, 102, 103, 104, 105, 106,107,108,109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 400, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1500 mg or any range derivable therein.

C. Partial Opioid Agonists/Antagonists

Buprenorphine effectively relieves moderate to severe pain in doses of 5 mcg (0.005 mg) mg or more administered either parenterally, sublingually, bucally or transdermally. Therapeutic range for single doses is reported as 0.3 mg-0.6 mg by injection and 0.1 mg-0.4 mg for sublingual tablets and 5 mcg-80 mcg for transdermal administration. Doses ranging from 2 mg a day to 32 mg a day are used sublingually when buprenorphine is used to treat chronic pain, opioid use disorder and/or opioid withdrawal.

Buprenorphine dosing varies depending on the formulation, tablets or film, for sublingual or buccal or transdermal administration. Typical sublingual dosing of buprenorphine for opioid use disorder is between 16 mg and 24 mg a day. One study found a reduction in suicidal thinking among severely suicidal patients without substance abuse with ultra-low-dose sublingual buprenorphine starting at 0.1 mg once or twice daily and titrated to a mean dose of 0.44 mg a day (Yoram Yovell et al. 2016).

The compositions disclosed herein are used in pharmaceutical formulations in pharmacologically effective amounts. In an embodiment, the amount of pharmaceutical composition administered is set to deliver a therapeutically effective amount of the partial opioid agonist, and/or buprenorphine, that is at least, or is at most about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg (or about any range derivable therein).

D. Ratios of Cannabinoid to Partial Opioid Agonist

The components partial opioid agonists and cannabinoids may be formulated in a particular ratio. In certain embodiments, the formulation may comprise the components in the following exemplary ratios of a purified cannabinoid and a partial opioid agonist of about: 1:1, 2:1, 3:1, 4:1, 5:1, 6:1, 7:1, 8:1, 9:1, 10:1, 12:1, 15:1, 20:1, 25:1, 30:1, 35:1, 40:1, 45:1, 50:1, 55:1, 60:1, 65:1, 70:1, 75:1, 80:1, 85:1, 90:1, 95:1, 100:1, 150:1, 200:1, 300:1, 400:1, 500:1, 600:1, 750:1, 800:1, 900:1, 1000:1, 2000:1, 3000:1, 4000:1, 5000:1, 6000:1, 7000:1, 8000:1, 9000:1, 10,000:1, 11,000:1, 12,000:1, 13,000:1, 14,000:1, 15,000:1, 16,000:1, 17,000:1, 18,000:1 and any derivable ratio in between. In certain embodiments, the ratios are 10:1, 20:1, 30:1, 40:1, 50:1, 60:1, 70:1, 80:1, 90:1 or 100:1, 200:1, 300:1, 400:1, 500:1, 600:1, 700:1, 800:1, 900:1, 1,000:1, 1,100:1, 1,200:1, 1,300:1, 1,400:1, 1,500:1, 1,600:1, 1,700:1, 1,800:1, 1,900:1, 2,000:1, 2,200:1, 2,400:1, 2,600:1, 2:800:1, 3,000:1, 3,200:1, 3,400:1, 3,600:1, 3,800:1, 4,000:1, 4,200:1, 4,400:1, 4,600:1, 4,800:1, 5,000:1, 5,200:1, 5,400:1, 5,600:1, 5:800:1, 6,000:1, 6,200:1, 6,400:1, 6,600:1, 6,800:1, 7,000:1, 7,200:1, 7,400:1, 7,600:1, 7,800:1, 8,000:1, 8,200:1, 8,400:1, 8,600:1, 8,800:1, 9,000:1, 9,200:1, 9,400:1, 9,600:1, 9,800:1, 10,000:1, 10,200:1, 10,400:1, 10,600:1, 10,800:1, 11000:1, 11,200:1, 11,400:1, 11,600:1, 11,800:1, 12,000:1, 12,200:1, 12,400:1, 12,600:1, 12,800:1, 13,000:1, 13,200:1, 13,400:1, 13,600:1, 13,800:1, 14,000:1, 14,200:1, 14,400:1, 14,600:1, 14,800:1, 15,000:1, 15,200:1, 15,400:1, 15,600:1, 15,800:1, 16,000:1, 16,200:1, 16,400:1, 16,600:1, 16,800:1, 17,000:1, 17,200:1, 17,400:1, 17,600:1, 17,800:1, 18,000:1, 18,200:1, 19,000:1, 20,000:1, or any ratio in between. In particular embodiments, the formulation may comprise the components in the following percentages by formulation (either the same or different percentages for each): 1%, 2%, 3%, 4%, 5%, 6%, 7%, 8%, 9%, 10%, 12%, 15%, 20%, 25%, 30%, 40%, 45%, 50%, 55%, 60%, 65%, 70%, 75%, 80%, 85%, 90%, 95%, 97%, or 99%, for example.

In embodiments, a sublingual tablet includes, for example, 2-900 mg purified cannabdiol, 0.005-50 mg/tablet buprenorphine HCL, 0.01-12.5 mg naloxone in addition to other excipients such as lactose, mannitol, maize starch, povidone, magnesium stearate and others for example.

In embodiments, a sublingual tablet includes, for example, 10 mg purified cannabidiol, 0.5 mg/tablet buprenorphine HCL in addition to other excipients such as lactose, mannitol, maize starch, povidone, magnesium stearate and others for example.

In embodiments, a sublingual tablet includes, for example, 10 mg purified cannabidiol, 0.5 mg/tablet buprenorphine HCL, 0.1-8 mg naloxone in addition to other excipients such as lactose, mannitol, maize starch, povidone, magnesium stearate and others for example.

In embodiments, a sublingual tablet includes, for example, 30 mg purified cannabidiol, 0.5 mg/tablet buprenorphine HCL, 0.1-8 mg naloxone in addition to other excipients such as lactose, mannitol, maize starch, povidone, magnesium stearate and others for example.

In embodiments, a sublingual tablet includes, for example, 50 mg purified cannabidiol, 0.5 mg/tablet buprenorphine HCL, 0.1-8 mg naloxone in addition to other excipients such as lactose, mannitol, maize starch, povidone, magnesium stearate and others for example.

In embodiments, a sublingual tablet includes, for example, 2-900 mg purified cannabidiol, 0.005-50 mg/tablet buprenorphine HCL, 0.01-12.5 mg naloxone in addition to other excipients such as lactose, mannitol, maize starch, povidone, magnesium stearate and others for example.

In additional embodiments a composition comprises 1) a cannabinoid, cannabidiol, a cannabidiol homologue, a cannabidiol derivatives, cannabidivarin or a 5-HT1A partial agonist that is, at least, or is at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100, 101, 102, 103, 104, 105, 106, 107, 108, 109, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 400, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1500 mg or any range derivable therein in combination with one or both of 2) a partial opioid agonist, or buprenorphine, that is at least, or is at most about 0.05, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg (or about any range derivable therein) and 3) an opioid antagonist (for example naltrexone, naloxone, nalmefene, nalide, nalmexone, nalorphine, nalorphine dinicotinate, cyclazocine, levallorphan, pharmaceutically acceptable salts thereof) that is, at least, or is at most about 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg (or about any range derivable therein). The composition may contain non-active ingredients or excipients such as lactose, mannitol, maize starch, povidone, magnesium stearate and others for example.

E. Opioid Antagonist

Opioid antagonists useful in the present invention include, for example naltrexone, naloxone, nalmefene, nalide, nalmexone, nalorphine, nalorphine dinicotinate, cyclazocine, levallorphan, pharmaceutically acceptable salts thereof, and mixtures thereof. In certain preferred embodiments, the opioid antagonist is naloxone or naltrexone. In certain embodiments, the amount of the opioid antagonist included in the dosage form, may be about 0.1-20 mg.

In an embodiment, the amount of pharmaceutical composition administered is set to deliver a therapeutically effective amount of an opioid antagonist that is, at least, or is at most about 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg (or about any range derivable therein).

V. Drug Synergy

The current combination compositions, formulations, preparations and methods of treating opioid use disorders, opioid withdrawal symptoms and chronic pain exploit the synergy between a cannabinoid and a partial opioid agonist. Drug synergy occurs in a combination dosage, or through either a concurrent drug administration or a sequential administration. The current combination of a purified cannabinoid with a partial opioid agonist has the potential to be more effective and safer than either compound alone. The combination of cannabidiol and buprenorphine, as way of example, works in synergy to enhance the anxiolytic effects of CBD and/or the analgesic and anti-opioid craving/withdrawal effects of buprenorphine. Furthermore, both CBD and buprenorphine are metabolized by Cytochrome P450 3A4 (CYP 3A4) enzymes and CBD also inhibits CYP 3A4 in an in vitro study. Concomitant administration of CBD and buprenorphine may reduce buprenorphine metabolism thereby achieving analgesic effects with lower doses of buprenorphine. We demonstrate that the effects of the combination of cannabidiol and a partial opioid agonist, here buprenorphine, are synergistic (greater than additive). We demonstrate that combining cannabidiol to a low dose of buprenorphine unexpectedly produces effects that are more than additive compared to effects for each of the components alone showing that a similar or greater effect can be obtained with lower, and safer, doses of buprenorphine when combined with cannabidiol.

In some embodiments, the current agents are used in a patient synergistically. The combination of the two agents: cannabinoid and a partial opioid agonist (for example, cannabidiol and buprenorphine) produces, in embodiments, an effect that is an improvement of 10, 15, 20, 25, 30, 35, 40, 45, 50, 55, 60, 65, 70, 75, 80, 85, 90, 95 or 100% or any range derivable therein as compared to using either agent alone or as compared to using other traditional compositions, or also as compared to no intervention. Alternatively synergy could produce an improvement of 1.5×, 2×, 2.5×, 3.0×, 3.5×, 4.0×, 4.5×, 5.0×, 5.5×, 6.0×, 6.5×, 7.0×, 7.5×, 8.0×, 8.5×, 9.0×, 9.5×, 10.0× (or any derivable range in between) compared to each agent alone. Alternatively, the combination of a cannabinoid with a partial opioid agonist may allow for similar clinical effects with lower, and therefore safer, doses of the partial opioid agonist.

Many measurable endpoints can be selected from which to define drug synergy, provided those endpoints are therapeutically relevant for elevation of chronic pain, opioid use disorders or opioid withdrawal symptoms. In certain embodiments, the improvement, for example, is the reduction in the amount of time that withdrawal symptoms are manifested, after the beginning of treatment. Alternatively, in some embodiments, improvements are manifested through the amelioration or cessation of one or more withdrawal symptoms such as but not limited to nausea, muscle cramping, depression, anxiety, agitation and opiate cravings. Yet in other situations, the improvement can be seen in the reduction of symptoms of sedation, vomiting, itching, flushed skin, respiratory depression, or episodes of euphoria. In other cases, the improvement can be seen in the reduction of opioid use such as in opioid use disorder. In other cases, the improvement can be seen in the reduction in the amount of pain intensity or pain interference or in the length of duration of pain intervals or in the frequency of occurrence of pain intervals. Improvement can also be manifested as a reduction in suicidal thinking. Improvement can also be manifested as overall enhanced functioning and quality of life.

VI. Other Combination Therapies

The compositions and related methods may also be used or combined with additional therapeutic agents or active ingredients or approaches that are currently used to treat opioid use disorders, opioid withdrawal symptoms or chronic pain or associated conditions. For example, the most common medical conditions associated with opioid use disorder are viral (e.g., HIV, hepatitis C virus) and bacterial infections, particularly among users of opioids by injection. Therefore, the compositions and related methods, particularly administration of a cannabinoid and a partial opioid agonist may also be used in combination with the administration of other traditional compositions or therapies used to fight infections. These include, but are not limited to anti-viral, anti-bacterial, anti-inflammatory, depression, anxiety, chronic pain syndrome, cognitive dysfunction, ADHD, insomnia, etc.

Alternatively, the compositions and related methods may precede or follow the other agent treatment by intervals ranging from minutes to weeks. In embodiments where the other agents or compositions are administered separately, one would generally ensure that a significant period of time did not expire between the time of each delivery, such that the therapeutic composition would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

Administration of the additional compositions to a patient/subject will follow general protocols for the administration of such compounds, taking into account the toxicity, if any, of the composition. It is expected that the treatment cycles would be repeated as necessary. It is also contemplated that various standard therapies, such as hydration, for example, may be applied in combination with the described therapy.

VII. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

The following example is to determine if BUP+CBD combination reduces pain more than BUP or CBD alone in a rodent model of chronic pain, the following experiment. (Christoph, Kogel et al. 2005) and (Costa, Trovato et al. 2007). The following models of chronic pain is an example that can or will be used:

1. Chronic constriction injury of the sciatic nerve model (neuropathic pain): Painful unilateral neuropathy will be induced by chronic constriction injury of the sciatic nerve in the right hind paw, according to Bennett and Xie (1988). Briefly, the animals will be anesthetized with sodium pentobarbital (60 mg/kg, i.p.). The right sciatic nerve will be exposed at mid-thigh level through a small incision, and one-third to one half of the nerve thickness will be loosely ligated with four silk threads. The wound will be closed with muscle suture and skin clips and dusted with streptomycin powder. In parallel surgery, the nerve was exposed but not ligated (sham operated rats).

2. Complete Freund's adjuvant model (inflammatory pain): 0.1 ml complete Freund's adjuvant containing 0.1 mg of *Mycobacterium tuberculosis* heat killed, 0.085 ml paraffin oil and 0.015 ml mannide monooleate (Sigma Aldrich, Milan, Italy) will be injected s.c. into the plantar side of right hind paw. Control rats received an intraplantar (i.pl.) injection of the same volume of saline.

The anti-hyperalgesic effects of BUP+CBD versus BUP and/or CBD alone will be assessed via:

1. Mechanical hyperalgesia: Mechanical hyperalgesia will be measured using a Randall Selitto analgesimeter (Ugo Basile, Varese, Italy). Latencies to withdrawal in response to a calibrated pressure will be assessed on the ligated/inflamed and contralateral hind paws on day 0 (before surgery and i.pl. injection) and again on day 7 (before starting the drug treatment) and on day 14 (24 h after the last dose). Cut-off will be set at 150 g.

2. Thermal hyperalgesia: Thermal hyperalgesia using a Hargreaves apparatus (Ugo Basile, Varese, Italy). Before the experiments, the animals will be placed in a transparent Perspex box with a thin glass floor and allowed to acclimatize for 10-15 min. A focused beam of radiant heat will be applied to the plantar surface and latencies to withdrawal will be assessed on the ligated/inflamed and contralateral hind paws on day 0 (before surgery and i.pl. injection) and again on day 7 (before starting the drug treatment) and on day 14 (24 h after the last dose). Cut-off will be set at 33 s.

The following drugs will be used for the study:

1. Cannabidiol, dissolved in methanol; after drying off the methanol under speed-vacuum, the pure cannabidiol residue will be emulsified in vehicle: cremophor, ethanol and saline (1:1:18); and 2. Buprenorphine hydrochloride will be dissolved in 0.9% NaCl. Buprenorphine will be administered IV in a volume of 5 ml/kg in rats.

Examples of doses that will be investigated include: 1) BUP 0.01 mg/kg; 2) CBD 20 mg/kg, and 3) BUP 0.01 mg/kg+CBD 20 mg/kg. Eight rats will be tested for each dose and with the mechanical and thermal hyperalgesia models. With 8 rats/dose×3 doses×2 hyperalgesia models=48 rats total.

Male Wistar rats (Table 1) will undergo baseline assessment of mechanical or thermal hyperalgesia (different animals will be used for each) and then undergo chronic constriction injury of the sciatic nerve (neuropathic pain model) or treatment with complete Freund's adjuvant (inflammatory pain model). Seven days after injury, rats will undergo re-assessment of mechanical or thermal hyperalgesia and then begin treatment with compound (BUP, CBD, or BUP+CBD) once daily for 7 days. Following completion of 7 days of treatment with experimental compound, rats with again undergo assessment of mechanical or thermal hyperalgesia.

Mechanical or thermal hyperalgesia following treatment with BUP, CBD, and BUP+CBD following chronic constriction injury of the sciatic nerve (neuropathic pain model) or treatment with complete Freund's adjuvant (inflammatory pain model) will be compared. We hypothesize that reductions in mechanical and thermal hyperalgesia will be greatest with the BUP+CBD combinations and that adding CBD to BUP will produce similar analgesic effects with lower doses of BUP. Outcome variable will be mean latency to withdraw for the mechanical and thermal hyperalgesia tests for BUP, CBD, and BUP+CBD, Example 2

Patients with chronic non-cancer pain who are not on opioids will be recruited to participate in this study. Each participant will undergo a baseline assessment of pain (Brief Pain Inventory), mood (anxiety and depression using the Hospital Anxiety and Depression Scale), and pain catastrophizing (3 item daily pain catastrophizing scale). After the intitial assessment, participants receive a CBD-BUP sublingual combination doses, such as, for example, 10 mg CBD and 0.005-50 mg BUP. Pain, mood, and catastrophizing will be re-assessed after acute dosing of CBD-BUP. Mean changes from pre-post CBD-BUP dosing in pain, mood, and catastrophizing will be calculated. After a period of post-dose observation, participants will be discharged home and study participation will be complete.

Example 3

The method of Example 2 will be repeated with a similar type of patient cohort, but with a CBD-BUP combination dose of 30 mg CBD and 0.5 mg BUP. Pain, mood, and catastrophizing will also be re-assessed after acute dosing of CBD-BUP. Mean changes from pre- to post-CBD-BUP dosing in pain, mood, and catastrophizing will be calculated.

Example 4

The method of Example 2 will also be repeated with a sublingual combination dose of CBD 50 mg and BUP 0.5 mg. Pain, mood, and catastrophizing will be re-assessed after acute dosing of CBD-BUP. Mean changes from pre- to post-CBD-BUP dosing in pain, mood, and/or catastrophizing will be calculated.

Example 5

Potential synergistic analgesic and opioid sparing effects of the combination of low dose buprenorphine and cannabidiol were evaluated in a preclinical proof-of-concept study. The inventors hypothesized that the combination of low dose buprenorphine and cannabidiol (low BUP-CBD) would produce similar or greater analgesic effects than standard analgesic doses of buprenorphine (BUP).

Male Sprague Dawley rats underwent baseline measurement of pain threshold via Von Frey testing according to the study schema in FIG. 4. The following day, rats underwent surgical ligation of the sciatic nerve using the Chronic Constriction Injury model of chronic neuropathic pain. After 7 days to allow the development of chronic neuropathic pain, rats underwent repeat Von Frey testing to determine pain threshold and started oral treatment with CBD or saline (Table 2). After 7 days of CBD or saline, rats underwent pre-dosing pain threshold determination via Von Frey testing and then received either standard dose BUP, low dose BUP, CBD alone or low dose BUP plus CBD followed by repeat post-dose pain threshold determination via Von Frey testing (Table 3).

Figure 5:
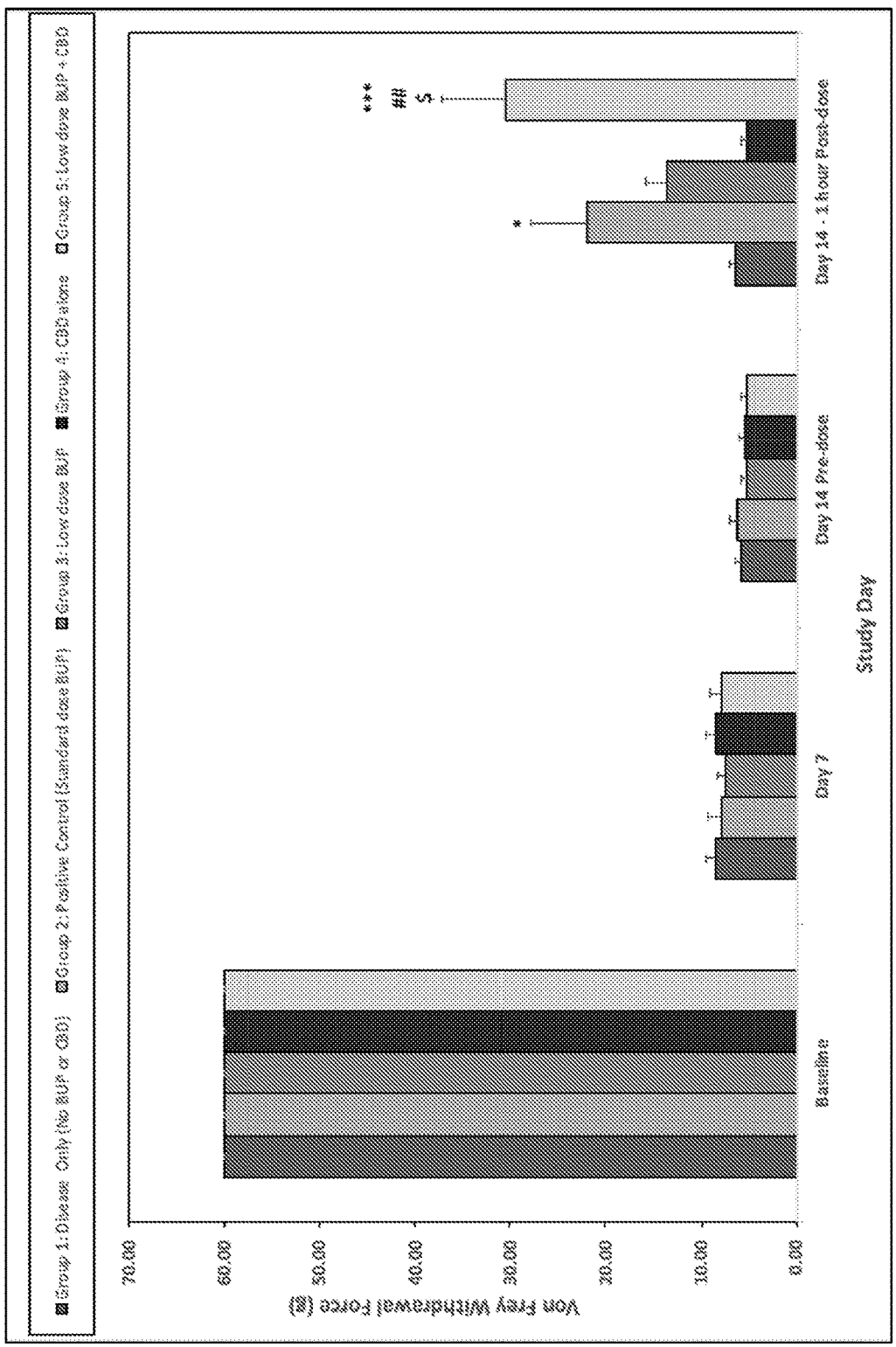
FIG. 5 is a graph in accordance with the current invention depicting pain threshold results following treatment with standard dose BUP, low dose BUP alone, CBD alone, and the combination of low dose BUP plus CBD.

Pain threshold was lower in all groups following sciatic nerve injury and initiation of the Chronic Constriction Injury model as evidenced by the lower threshold on Von Frey testing on day 7 compared to baseline (FIG. 5). On day 14, standard dose BUP significantly increased pain threshold compared to no BUP (Group 1) while low dose BUP and CBD alone did not significantly increase pain threshold. The combination of low dose BUP and CBD significantly increased pain threshold and the combination produced a greater increase in pain threshold compare to no BUP (Group 1) and to either compound alone (Group 3 and 4). Furthermore, the mean pain threshold for the low dose BUP plus CBD combination, 30.38 g, was higher than the sum of the pain thresholds for low dose BUP alone (13.50 g) and CBD alone (5.25 g) demonstrating that the combination of low dose BUP and CBD produced analgesic effects that were synergistic (greater than additive).

TABLE 1

Study Schema for Examples 1-4

| Study Day | Procedures/Treatments |
|---|---|
| 0 | Baseline assessment of mechanical/thermal hyperalgesia Chronic constriction injury of the sciatic nerve (neuropathic pain model) or treatment with complete Freund's adjuvant (inflammatory pain model) |
| 1-6 | No treatments |
| 7 | Repeat assessment of mechanical/thermal hyperalgesia Start once daily treatment with compound (BUP, CBD BUP + CBD) |
| 8-13 | Continue once daily treatment with compound (BUP, CBD, BUP + CBD) |
| 14 | Repeat assessment of mechanical/thermal hyperalgesia (24 hour after last dose of compound) |

TABLE 2

Treatment group assignments for Example 5

| N | Treatment | Route | Dose (mg/kg) | Regimen |
|---|---|---|---|---|
| 8 | Chronic pain only (No BUP, No CBD) | IV | NA | Saline once on day 14 |
|   |   | PO | NA | Saline on days 7-14 |
| 8 | Standard dose BUP | IV | 0.04 | BUP once on day 14 |
|   |   | PO | NA | Saline on days 7-14 |
| 8 | Low dose BUP | IV | 0.01 | BUP once on day 14 |
|   |   | PO | NA | Saline on days 7-14 |
| 8 | CBD alone | IV | NA | Saline once on day 14 |
|   |   | PO | 7 | CBD on days 7-14 |
| 8 | Low dose BUP plus CBD | IV | 0.01 | BUP once on day 14 |
|   |   | PO | 7 | CBD on days 7-14 |

TABLE 3

Mean pain threshold (g in Von Frey Testing) following treatment with standard dose BUP, low dose BUP alone, CBD alone, and the combination of low dose BUP plus CBD.

|  | Baseline | | Day 7 | | Day 14 Pre-Dose | | Day 14-1 hour Post Dose | |
|---|---|---|---|---|---|---|---|---|
| Treatment | Mean | SEM | Mean | SEM | Mean | SEM | Mean | SEM |
| Group 1: Disease Only (No BUP or CBD) | 60.00 | 0.00 | 8.38 | 1.19 | 5.75 | .059 | 6.50 | 0.63 |

TABLE 3-continued

Mean pain threshold (g in Von Frey Testing) following treatment with standard dose BUP, low dose BUP alone, CBD alone, and the combination of low dose BUP plus CBD.

| Treatment | Baseline | | Day 7 | | Day 14 Pre-Dose | | Day 14-1 hour Post Dose | |
|---|---|---|---|---|---|---|---|---|
| | Mean | SEM | Mean | SEM | Mean | SEM | Mean | SEM |
| Group 2: Positive Control (Standard dose BUP) | 60.00 | 0.00 | 7.88 | 1.32 | 6.25 | 0.70 | 21.88* | 5.92 |
| Group 3: Low Dose BUP | 60.00 | 0.00 | 7.50 | 0.73 | 5.25 | 0.65 | 13.50 | 2.24 |
| Group 4: CBD alone | 60.00 | 0.00 | 8.38 | 1.19 | 5.50 | 0.63 | 5.25 | 0.53 |
| Group 5: Low dose BUP + CBD | 60.00 | 0.00 | 7.88 | 1.20 | 5.25 | 0.53 | 30.38***##$ | 6.71 |

*$p < 0.01$ vs. Disease only (Group 1) using one way ANOVA followed by Dunnet's test.
***$p < 0.001$ vs. Disease only (Group 1) using one way ANOVA followed by Dunnet's test.
$p < 0.01$ vs. Group 4 using one way ANOVA followed by Tukey test
$$p < 0.05$ vs. Group 3 using one way ANOVA followed by Tukey test All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references recited in the application, to the extent that they provide exemplary procedural or other details supplementary to those set forth herein, are specifically incorporated herein by reference.

REFERENCES

The following references and the publications referred to throughout the specification, to the extent that they provide exemplary procedural or other details supplementary to those set forth herein, are specifically incorporated herein by reference.

Arteta, J., B. Cobos, Y. Hu, K. Jordan and K. Howard (2016). "Evaluation of How Depression and Anxiety Mediate the Relationship Between Pain Catastrophizing and Prescription Opioid Misuse in a Chronic Pain Population." *Pain Med* 17(2): 295-303.

Babu K. M, C. R. McCurdy, and E. W. Boyer. Opioid receptors and legal highs: *Salvia divinorum* and *Kratom*. Clin Toxicol (Phila). 2008 February; 46(2):146-52.

Christoph, T., B. Kogel, K. Schiene, M. Meen, J. De Vry and E. Friderichs (2005). "Broad analgesic profile of buprenorphine in rodent models of acute and chronic pain." *Eur J Pharmacol* 507(1-3): 87-98.

Costa, B., A. E. Trovato, F. Comelli, G. Giagnoni and M. Colleoni (2007). "The non-psychoactive *cannabis* constituent cannabidiol is an orally effective therapeutic agent in rat chronic inflammatory and neuropathic pain." *Eur J Pharmacol* 556(1-3): 75-83.

Crippa, J. A., G. N. Derenusson, T. B. Ferrari, L. Wichert-Ana, F. L. Duran, R. Martin-Santos, M. V. Simoes, S. Bhattacharyya, P. Fusar-Poli, Z. Atakan, A. Santos Filho, M. C. Freitas-Ferrari, P. K. McGuire, A. W. Zuardi, G. F. Busatto and J. E. Hallak (2011). "Neural basis of anxiolytic effects of cannabidiol (CBD) in generalized social anxiety disorder: a preliminary report." *J Psychopharmacol* 25(1): 121-130.

Crippa, J. A., A. W. Zuardi, G. E. Garrido, L. Wichert-Ana, R. Guarnieri, L. Ferrari, P. M. Azevedo-Marques, J. E. Hallak, P. K. McGuire and G. Filho Busatto (2004). "Effects of cannabidiol (CBD) on regional cerebral blood flow." *Neuropsychopharmacology* 29(2): 417-426.

Cunningham, J. L., J. R. Craner, M. M. Evans and W. M. Hooten (2017). "Benzodiazepine use in patients with chronic pain in an interdisciplinary pain rehabilitation program." *J Pain Res* 10: 311-317.

Edwards, R. R., A. J. Dolman, E. Michna, J. N. Katz, S. S. Nedeljkovic, D. Janfaza, Z. Isaac, M. O. Martel, R. N. Jamison and A. D. Wasan (2016). "Changes in Pain Sensitivity and Pain Modulation During Oral Opioid Treatment: The Impact of Negative Affect." *Pain Med.*

Garg, R. K., D. Fulton-Kehoe and G. M. Franklin (2017). "Patterns of Opioid Use and Risk of Opioid Overdose Death Among Medicaid Patients." *Med Care* 55(7): 661-668.

Graham, J. D. and D. M. Li (1973). "Cardiovascular and respiratory effects of *cannabis* in cat and rat." *Br J Pharmacol* 49(1): 1-10.

Gureje, O., M. Von Korff, G. E. Simon and R. Gater (1998). "Persistent pain and well-being: A world health organization study in primary care." JAMA 280(2): 147-151.

Kim, H., D. M. Hartung, R. L. Jacob, D. McCarty and K. J. McConnell (2016). "The Concentration of Opioid Prescriptions by Providers and Among Patients in the Oregon Medicaid Program." *Psychiatr Serv* 67(4): 397-404.

Larochelle, M. R., F. Zhang, D. Ross-Degnan and J. F. Wharam (2015). "Trends in opioid prescribing and co-prescribing of sedative hypnotics for acute and chronic musculoskeletal pain: 2001-2010." *Pharmacoepidemiol Drug Saf* 24(8): 885-892.

Martel, M. O., A. D. Wasan, R. N. Jamison and R. R. Edwards (2013). "Catastrophic thinking and increased risk for prescription opioid misuse in patients with chronic pain." *Drug Alcohol Depend* 132(1-2): 335-341.

Martins, S. S., A. Sarvet, J. Santaella-Tenorio, T. Saha, B. F. Grant and D. S. Hasin (2017). "Changes in US Lifetime Heroin Use and Heroin Use Disorder: Prevalence From the 2001-2002 to 2012-2013 National Epidemiologic Survey on Alcohol and Related Conditions." *JAMA Psychiatry* 74(5): 445-455.

McHugh, R. K., R. D. Weiss, M. Cornelius, M. O. Martel, R. N. Jamison and R. R. Edwards (2016). "Distress Intolerance and Prescription Opioid Misuse Among Patients With Chronic Pain." *J Pain* 17(7): 806-814.

Nielsen, S., N. Lintzeris, R. Bruno, G. Campbell, B. Larance, W. Hall, B. Hoban, M. L. Cohen and L. Degenhardt (2015). "Benzodiazepine use among chronic pain patients prescribed opioids: associations with pain, physical and mental health, and health service utilization." *Pain Med* 16(2): 356-366.

Pisanti, S., A. M. Malfitano, E. Ciaglia, A. Lamberti, R. Ranieri, G. Cuomo, M. Abate, G. Faggiana, M. C. Proto, D. Fiore, C. Laezza and M. Bifulco (2017). "Cannabidiol: State of the art and new challenges for therapeutic applications." *Pharmacol Ther.*

Stout, S. M. and N. M. Cimino (2014). "Exogenous cannabinoids as substrates, inhibitors, and inducers of human drug metabolizing enzymes: a systematic review." *Drug Metab Rev* 46(1): 86-95.

Terry, M. J., S. M. Moeschler, B. C. Hoelzer and W. M. Hooten (2016). "Pain Catastrophizing and Anxiety are Associated With Heat Pain Perception in a Community Sample of Adults With Chronic Pain." *Clin J Pain* 32(10): 875-881.

Toth, A. R., C. J. Possidente, L. M. Sawyer, M. A. DiParlo and G. J. Fanciullo (2016). "National and Northern New England Opioid Prescribing Patterns, 2013-2014." *Pain Med.*

Velly, A. M. and S. Mohit (2017). "Epidemiology of pain and relation to psychiatric disorders." *Prog Neuropsychopharmacol Biol Psychiatry.*

Wasan, A. D., E. Michna, R. R. Edwards, J. N. Katz, S. S. Nedeljkovic, A. J. Dolman, D. Janfaza, Z. Isaac and R. N. Jamison (2015). "Psychiatric Comorbidity Is Associated Prospectively with Diminished Opioid Analgesia and Increased Opioid Misuse in Patients with Chronic Low Back Pain." *Anesthesiology* 123(4): 861-872.

Wertli, M. M., R. Eugster, U. Held, J. Steurer, R. Kofmehl and S. Weiser (2014). "Catastrophizing-a prognostic factor for outcome in patients with low back pain: a systematic review." *Spine J.*

Yoram Yovell, Gali Bar, Moti Mashiah, Yehuda Baruch, Irina Briskman, Jack Asherov, Amit Lotan, Amihai Rigbi and Jaak Panksepp (2016). "Ultra-Low-Dose Buprenorphine as a Time-Limited Treatment for Severe Suicidal Ideation: A Randomized Controlled Trial." *American Journal of Psychiatry* 173(5): 491-498.

Zuardi, A. W., N. P. Rodrigues, A. L. Silva, S. A. Bernardo, J. E. C. Hallak, F. S. Guimaraes and J. A. S. Crippa (2017). "Inverted U-Shaped Dose-Response Curve of the Anxiolytic Effect of Cannabidiol during Public Speaking in Real Life." *Front Pharmacol* 8: 259.

What is claimed is:

1. A method of treating opioid use disorder, opioid withdrawal symptoms, and/or chronic pain in a subject comprising administering to the subject cannabidiol and a partial opioid agonist, wherein cannabidiol and the partial opioid agonist are administered at a synergistically effective ratio of about 700:1 to 4,000:1, and wherein cannabidiol and the partial opioid agonist are administered sublingually.

2. The method of claim 1, wherein cannabidiol comprises purified cannabidiol, one or more pharmaceutically acceptable derivatives of cannabidiol, one or more pharmaceutically acceptable salts of cannabidiol, one or more cannabidiol prodrugs, one or more cannabidiol solvates, one or more cannabidiol metabolites, one or more cannabidiol metabolic precursors, or one or more cannabidiol homologues.

3. The method of claim 1, wherein the partial opioid agonist is buprenorphine, mitragynine or 7-hydroxymitragynine.

4. The method of claim 1, wherein cannabidiol and the partial opioid agonist are administered between 30 minutes and 24 hours of each other.

5. The method of claim 1, wherein cannabidiol and the partial opioid agonist are administered at the same time to the subject.

6. The method of claim 1, wherein cannabidiol and the partial opioid agonist are administered to the subject together in the same composition.

7. The method of claim 1, further comprising administering an opioid antagonist to the subject.

8. The method of claim 7, wherein the opioid antagonist is naloxone, an oxymorphol analog of naloxone, a naloxone salt, or a naloxone dihydrate.

9. The method of claim 7, wherein the opioid antagonist is naloxone.

10. The method of claim 7, wherein the opioid antagonist is naltrexone.

11. The method of claim 1, wherein the subject is administered from 2 mg to 900 mg of cannabidiol.

12. The method of claim 11, wherein the subject is administered from 7 mg to 200 mg of cannabidiol.

13. The method of claim 1, wherein the subject is administered from 0.005 mg to 50 mg of the partial opioid agonist.

14. The method of claim 13, wherein the subject is administered from 0.1 mg to 1 mg of the partial opioid agonist.

15. The method of claim 14, wherein the partial opioid agonist is buprenorphine, and wherein the subject is administered about 0.5 mg of buprenorphine.

16. The method of claim 1, wherein cannabidiol and the partial opioid agonist are administered multiple times over the course of at least 1 week.

17. A pharmaceutical composition comprising cannabidiol and a partial opioid agonist, wherein cannabidiol and the partial opioid agonist comprise a synergistically effective ratio of about 700:1 to 4,000:1 and wherein the composition is formulated for sublingual administration.

18. The pharmaceutical composition of claim 17, further comprising an opioid antagonist.

19. The pharmaceutical composition of claim 17, wherein the partial opioid agonist is buprenorphine.

20. The pharmaceutical composition of claim 19, wherein the composition comprises from about 10 mg to about 30 mg cannabidiol and about 0.5 mg buprenorphine.

21. The pharmaceutical composition of claim 19 further comprising naloxone.

22. The method of claim 7, wherein:
cannabidiol is administered at a dose of from about 2 mg to about 900 mg;
the partial opioid agonist is buprenorphine and is administered at a dose of from about 0.005 mg to about 50 mg; and
the opioid antagonist is naloxone and is administered at a dose of from about 0.01 mg to about 12.5 mg.

* * * * *